United States Patent
Yu et al.

(10) Patent No.: US 6,861,523 B2
(45) Date of Patent: Mar. 1, 2005

(54) 1,3,5- TRISUBSTITUTED-1,3,5-TRIAZINE-2,4, 6-TRIONE COMPOUNDS AND LIBRARIES

(75) Inventors: Yongping Yu, San Diego, CA (US); John M. Ostresh, Encinitas, CA (US); Richard A. Houghten, DelMar, CA (US)

(73) Assignee: Torrey Pines Institute for Molecular Studies, San Diego, CA (US)

( * ) Notice: Subject to any disclaimer, the term of this patent is extended or adjusted under 35 U.S.C. 154(b) by 76 days.

(21) Appl. No.: 10/071,707

(22) Filed: Feb. 8, 2002

(65) Prior Publication Data

US 2003/0186320 A1 Oct. 2, 2003

(51) Int. Cl.[7] ............................................. C07D 251/00
(52) U.S. Cl. ........................ 544/222; 544/221; 514/241
(58) Field of Search .......................... 514/241; 544/221, 544/222

(56) References Cited

U.S. PATENT DOCUMENTS

| | | | |
|---|---|---|---|
| 4,053,538 A | * 10/1977 | Herweh et al. ............. | 525/444 |
| 4,631,211 A | 12/1986 | Houghten | |
| 5,143,854 A | 9/1992 | Pirrung et al. | |
| 5,182,366 A | 1/1993 | Huebner et al. | |
| 5,367,053 A | 11/1994 | Dooley et al. | |
| 5,556,762 A | 9/1996 | Pinilla et al. | |
| 5,679,791 A | * 10/1997 | Crews et al. ............... | 544/222 |

FOREIGN PATENT DOCUMENTS

| | | |
|---|---|---|
| DE | 1927921 | 12/1970 |
| DE | 2718799 | 11/1978 |
| DE | 3516631 | 11/1986 |
| DE | 3516632 | 11/1986 |
| EP | 364765 | 4/1990 |
| WO | WO 84/03564 | 9/1984 |
| WO | WO 91/08694 | 6/1991 |
| WO | WO 92/09300 | 6/1992 |

OTHER PUBLICATIONS

Yu et al., "Efficient Solid–Phase Synthesis of 1,3,5–Trisubstituted 1,3,5–Triazine–2,4,6–triones", *J. Comb. Chem.*, vol. 4(5), 484–490 (2002).
Hall et al. *J. Comb. Chem.* (2001) 3(2):125–150.
Wendeborn et al. *S. Acc. Chem. Res.* (2000) 33:215–224.
Houghten et al. *J. Med. Chem.* (1999) 42(19):3743–3778.
Brown *J. Chem. Soc., Perkin Trans. I* (1998) 3293–3320.
Hermkens et al. *Tetrahedron* (1997) 53(16):5643–5678.
Balkenhohl et al. *Angew. Chem. Int. Ed. Engl.* (1996) 35:2288–2337.
Thompson et al, *Chem. Rev.* 1996, 96:555–600.
Nefzi et al. *Chem. Rev.* (1997) 97:449–472.
Fruchtel et al. *Angew. Chem.,Int. Ed. Engl.* 1996, 35:17–42.
Franzen, R.G. *Comb. Chem.* (2000) 2(3):195–214.
Hempel et al. *J. Med. Chem.* (1989) 32:648–651.
Atassi et al. *Europ. J. Cancer* (1980) 16:1561–1567.
Wu et al. *Mol. Pharmacol.* (1983) 23:182–189.
Haberkorn et al., *VMR, Vet. Med. Rev.* (1987) 1:22–32; *Chem. Abst.* (1998) 108, 15842Y.
Kogon, *J. Am. Chem. Soc.* (1956) 78:4911–4914.
Tang et al., *J. Org. Chem.* (1994) 59:4931–4938.
Kogon *J. Org. Soc.* (1959) 24:83–86.
Nambu et al. *J. Org. Chem.* (1993) 58:1932–1934.
Herbstman *J. Org. Chem.* (1965) 30:1259–1260.
Flamini *Tetrahedron Lett.* (1987) 28(19):2169–2170.
Ostresh et al. *J. Org. Chem.* (1998) 63:8622–8623.
Yu et al. *Org. Lett.* (2001) 3(18):2797–2799.
Acharya et al. *J. Comb. Chem.* (2001) 3:189–195.
Houghten et al. *Nature* (1991) 354:84–86.
Dooley et al. *Science* (1994) 266:2019–2022.
Houghten *Proc. Natl. Acad. Sci. USA* (1985) 82:5131–5135.
Nefzi et al. *Tetrahedron* (1999) 55:335–344.
Kaiser et al. *Anal. Biochem.* (1970) 34:595–598.
Gopalsamy et al. *J. Comb. Chem.* (2001) 3:278–283.
Rano et al. *Tetrahedron Lett.* (1995) 36(22):3789–3792.
Albericio et al. *J. Comb. Chem.* (2001) 3:290–300.
Ostrech et al. *Proc. Natl. Acad. Sci. USA* (1994) 91:11138–11142.
Houghten et al. *Int. J. Pept. Protein Res.* (1986) 27:673–678.
Dooley et al. *J. Biol. Chem.*, (1998) 273(30):18848–18856.
Bradford *Anal. Biochem.*, (1976) 72:248–254.
Lahti et al. *European J. Pharmacol.* (1985) 109:281–284.
Lahti et al. *Life Sci.,* (1982) 31:2257–2260.
Von Voightlander et al. *J. Pharmacol. Exp. Ther.* (1983) 224(1):7–12.
Yu et al. *Tetrahedron Lett.* (2001) 42, 623.

\* cited by examiner

*Primary Examiner*—Bennett Celsa
*Assistant Examiner*—Jon D. Epperson
(74) *Attorney, Agent, or Firm*—Welsh & Katz, Ltd.

(57) ABSTRACT

The solid-phase synthesis of individual 1,3-disubstituted and 1,3,5-trisubstituted-1,3,5-triazine-2,4,6-triones and libraries thereof from a resin is described. Reaction of resin-bound amino acids with isocyanates yields resin-bound ureas, which further react with chlorocarbonyl isocyanate to selectively afford the resin-bound 1,3-disubstituted-1,3,5-triazine-2,4,6-triones. Selective alkylation at the N-5 position of the resin-bound 1,3-disubstituted-1,3,5-triazine-2,4, 6-triones produces a trisubstituted triazinetrione. The products are cleaved from their solid support and obtained in good yield and purity.

8 Claims, No Drawings

1,3,5-TRISUBSTITUTED-1,3,5-TRIAZINE-2,4,6-TRIONE COMPOUNDS AND LIBRARIES

GOVERNMENTAL SUPPORT

This invention was made with governmental support pursuant to National Cancer Institute Grant No. CA78040. The government has certain rights in the invention.

BACKGROUND ART

Solid-phase techniques for the synthesis of peptides have been extensively developed and combinatorial libraries of peptides have been prepared with great success. There has been substantial development of chemically synthesized combinatorial libraries (SCLs) made up of peptides in the last decade.

The preparation and use of synthetic peptide combinatorial libraries has been described for example by Dooley in U.S. Pat. No. 5,367,053; Huebner in U.S. Pat. No. 5,182,366; Appel et al in PCT WO 92/09300; Geysen in published European Patent Application 0 138 855 and Pimmg in U.S. Pat. No. 5,143,854. Such peptide SCLs provide the efficient synthesis of an extraordinary number of various peptides in such libraries and the rapid screening of the library that identifies lead pharmaceutical peptides.

Peptides have been, and remain, attractive targets for drug discovery. Their high affinities and specificities toward biological receptors as well as the ease with which large peptide libraries can be combinatorially synthesized make them attractive drug targets. The screening of peptide libraries has led to the identification of many biologically-active lead compounds. However, the therapeutic application of peptides is limited by their poor stability and bioavailability in vivo. Therefore, there is a need to synthesize and screen compounds that can maintain high affinity and specificity toward biological receptors, while exhibiting improved pharmacological properties relative to peptides. Combinatorial approaches have recently been extended to "organic" or non-peptide libraries.

Combinatorial organic synthesis on solid supports has thus emerged as an important tool in lead structure identification and optimization in drug discovery. [For reviews, see: (a) Hall et al., J. Comb. Chem. 2001, 3, 125; (b) Wendeborn et al., S. Acc. Chem. Res. 2000, 33, 215; (c) Houghten et al., J. M. J. Med. Chem. 1999, 42, 3743; (d) Brown, J. Chem. Soc., Perkin Trans. 1 1998, 3293; (e) Hermkenset al., Tetrahedron 1997, 53, 5643; (f) Balkenhohl et al., Angew. Chem., int. Ed. Engl. 1996, 35, 2288; (g) Thompson et al., Chem. Rev. 1996, 96, 555; and Thompson et al., J. A. Chem. Rev. 1996, 96, 555.] The focus of this field of research is now on the synthesis of small organic molecules on the solid-phase. [(a) Nefzi et al., Chem. Rev. 1997, 97, 449; and b) Fruchtel et al., Angew. Chem., int. Ed. Engl. 1996, 35, 17.] Heterocyclic compounds have received special attention in combinatorial synthesis due to their high degree of structural diversity and biologically interesting properties. [Robert, J. Comb. Chem. 2000, 2, 195.]

Triazinetriones are an important class of molecules with pharmaceutical [(a) Hempel et al., J. Med. Chem. 1989, 32, 648; (b) Atassi et al., Eur. J. Cancer 1980, 16, 1561. (c) Wu et al., Mol. Pharmacol. 1983, 23, 182.] and agricultural [(a) Hagemann, Ger. Offen. 1 927 (1970); C. A. 1971, 74, 42392; and (b) Lindner et al., European Patent Application EP 364 765 (1990); C. A. 1990, 113, 152470.] utility including effective herbicides [Hagemann, Ger. Offen. 1 927 (1970); C. A. 1971, 74, 42392], drugs against coccidosis [Lindner et al., European Patent Application EP 364 765 (1990)] and animal growth stimulators. [Haberkorn, A.; Scheer, M.; Stoltefuss, J. Ger. Offen. 2 718 799(1978); C. A. 1979, 90, 104020.]

An example of such biologically interesting triazinetrione derivatives is Toltrazuril (shown below). This compound has coccidiocidal action

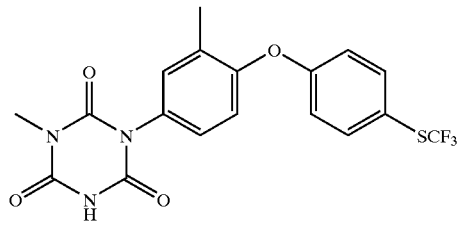

and damages all intracellular developmental stages of the schizogony cycles and of the gametogony phase and is an approved anticoccidial therapeutic. [Haberkorn et al., VMR, Vet. Med. Rev. 1987, 1, 22; C. A. 1988, 108, 15842.]

Symmetrically trisubstituted triazinetriones have previously been synthesized in solution from isocyanates by a broad range of catalysts such as Lewis acid [(a) Kogon, J. Am. Chem. Soc. 1956, 78, 4911; and (b) Tang et al., J. Org. Chem. 1994, 59, 4931], anions [(a) Kogon, J. Org. Chem. 1959, 24, 83; and (b) Nambu et al., J. Org. Chem. 1993, 58, 1932], and organometallics [(a) Herbstman, J. Org. Chem. 1965, 30, 1259; and (b) Flamini, Tetrahedron Lett. 1987, 28, 2169]. However, most of these conventional methods require severe conditions and are not suitable for solid-phase synthesis. Other approaches to the synthesis of substituted triazinetriones are found in the patent literature [(a) Hagemann, Ger. Offen. 1 927 921(1970); C. A. 1971, 74, 42392; (b) Gallenkamp et al., Ger. Offen. 3 516 632(1986); C. A. 1987, 106, 67355; and (c) Lantzsch, Ger. Offen. 3 516 631(1986); C. A. 1987, 106, 67356] in which, such compounds are prepared by the cyclocondensation of isocyanate with ureas and diethyl carbonate or ureas are cyclocondensed with chlorocarbonyl isocyanate.

It is therefore clear that prior art syntheses of triazinetriones are in need of improvement. The disclosure that follows is directed to new triazinetriones. That disclosure further extends the combinatorial solid phase synthesis of individual small heterocyclic molecules to include triazinetriones and libraries thereof using amino acids as starting materials [(a) Ostresh et al., J. Org. Chem. 1998, 63, 8622; (b) Yu et al., Tetrahedron Lett. 2001, 42, 623; (c) Yu et al., Organic Letters. 2001, 3, 2797; and (d) Acharya et al., J. Comb. Chem. 2001, 3, 189] through the use of techniques that help overcome the several disadvantages in the prior syntheses of such compounds.

BRIEF SUMMARY OF THE INVENTION

One aspect of the present invention contemplates a single compound or library of compounds having a structure corresponding to that shown in Formula I, below, or a pharmaceutically acceptable salt thereof:

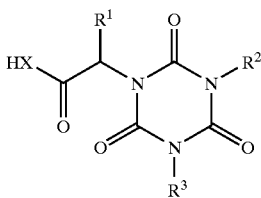

wherein:

X is O or NH;

R¹ is selected from the group consisting of a hydrido, $C_1$–$C_{10}$ alkyl, $C_1$–$C_{10}$ substituted alkyl, $C_7$–$C_{16}$ phenylalkyl, $C_7$–$C_{16}$ substituted phenylalkyl, phenyl, substituted phenyl, $C_3$–$C_7$ cycloalkyl, and a $C_3$–$C_7$ substituted cycloalkyl group;

R² is selected from the group consisting of a $C_1$–$C_{10}$ alkyl, $C_1$–$C_{10}$ substituted alkyl, $C_7$–$C_{16}$ phenylalkyl, $C_7$–$C_{16}$ substituted phenylalkyl, phenyl, substituted phenyl, $C_3$–$C_7$ cycloalkyl, $C_3$–$C_7$ substituted cycloalkyl, and a $C_3$–$C_7$ substituted cycloalkyl group; and R³ is selected from the group consisting of a hydrido, $C_1$–$C_{10}$ alkyl, $C_1$–$C_{10}$ substituted alkyl, $C_2$–$C_{10}$ alkenyl, $C_2$–$C_{10}$ substituted alkenyl, $C_2$–$C_{10}$ alkynyl, $C_2$–$C_{10}$ substituted alkynyl, $C_3$–$C_7$ cycloalkyl, $C_3$–$C_7$ substituted cycloalkyl, phenyl, $C_7$–$C_{16}$ phenylalkyl, $C_7$–$C_{16}$ phenylalkenyl, $C_7$–$C_{16}$ phenylalkenyl and a $C_7$–$C_{16}$ substituted phenylalkenyl group.

In preferred practice, a contemplated single compound or library of compounds has a structure corresponding to Formula IIA or IIB shown below,

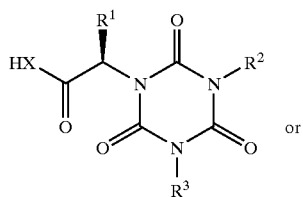

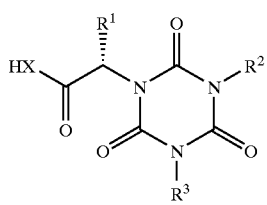

wherein a darkened, wedge-shaped line indicates a bond extending upwardly from the plane of the page whereas a dashed, wedge-shaped line indicates a bond extending downwardly below the plane of the page.

A process or method of forming a 1,3-disubstituted-2,4,6-triazinetrione is contemplated as another aspect of the invention. Such a process or method comprises the steps of:

a) providing an amino acid reversibly bound to a solid phase, the amino acid having a free amino group and a side chain denominated R¹;

b) reacting the amine of the solid phase bound amino acid with an R²-substituted isocyanate to form a solid phase-bound urea having R¹ and R² substituents;

c) reacting the solid phase-bound urea with chlorocarbonylisocyanate to form a 1,3-disubstituted-2,4,6-triazinetrione whose 1- and 3-substituents are R¹ and R², respectively; and d) cleaving said 1,3-disubstituted-2,4,6-triazinetrione from said solid support, wherein R¹ is selected from the group consisting of a hydrido, $C_1$–$C_{10}$ alkyl, $C_1$–$C_{10}$ substituted alkyl, $C_7$–$C_{16}$ phenylalkyl, $C_7$–$C_{16}$ substituted phenylalkyl, phenyl, substituted phenyl, $C_3$–$C_7$ cycloalkyl, and a $C_3$–$C_7$ substituted cycloalkyl group; and R² is selected from the group consisting of a $C_1$–$C_{10}$ alkyl, $C_1$–$C_{10}$ substituted alkyl, $C_7$–$C_{16}$ phenylalkyl, $C_7$–$C_{16}$ substituted phenylalkyl, phenyl, substituted phenyl, $C_3$–$C_7$ cycloalkyl, $C_3$–$C_7$ substituted cycloalkyl, and a $C_3$–$C_7$ substituted cycloalkyl group.

A process for preparing a 1,3,5-trisubstituted-2,4,6-triazinetrione is also contemplated. That process comprises alkylating the 1,3-disubstituted-2,4,6-triazinetrione of the previous synthesis prior to the cleaving step using an R³ group-containing alkylating agent, wherein R³ is selected from the group consisting of a hydrido, $C_1$–$C_{10}$ alkyl, $C_1$–$C_{10}$ substituted alkyl, $C_2$–$C_{10}$ alkenyl, $C_2$–$C_{10}$ substituted alkenyl, $C_2$–$C_{10}$ alkynyl, $C_2$–$C_{10}$ substituted alkynyl, $C_3$–$C_7$ cycloalkyl, $C_3$–$C_7$ substituted cycloalkyl, phenyl, $C_7$–$C_{16}$ phenylalkyl, $C_7$–$C_{16}$ phenylalkenyl, $C_7$–$C_{16}$ phenylalkenyl and a $C_7$–$C_{16}$ substituted phenylalkenyl group.

The present invention has several benefits and advantages. One benefit is the provision of a new synthesis for 1,3-disubstituted- and 1,3,5-trisubstituted-2,4,6-triazinetrione compounds. The present invention provides a large array of diverse 1,3-disubstituted- and 1,3,5-trisubstituted-2,4,6-triazinetrione compounds that can be screened for biological activity, and as described below, are biologically active.

An advantage of the invention is that individual compounds can be prepared or libraries containing a plurality of compounds can be prepared.

Another benefit of the invention is that the yield of 1,3-disubstituted- or 1,3,5-trisubstituted-2,4,6-triazinetrione compounds produced is relatively great compared to that obtained in prior syntheses of the parental compound.

Still further benefits and advantages of the invention will be apparent to the skilled worker from the discussion that follows.

DETAILED DESCRIPTION OF THE INVENTION

The present invention relates to the preparation and use of synthetic combinatorial libraries and individual 1,3-disubstituted- and 1,3,5-trisubstituted-1,3,5-triazine-2,4,6-trione compounds also referred to as more simply as triazinetrione compounds or the like that correspond in structure to Formula I, and their pharmaceutically-acceptable salts:

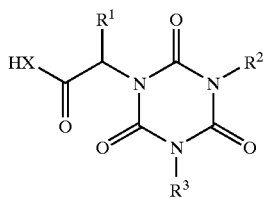

I wherein:

X is O or NH;

$R^1$ is selected from the group consisting of a hydrido, $C_1$–$C_{10}$ alkyl, $C_1$–$C_{10}$ substituted alkyl, $C_7$–$C_{16}$ phenylalkyl, $C_7$–$C_{16}$ substituted phenylalkyl, phenyl, substituted phenyl, $C_3$–$C_7$ cycloalkyl, and a $C_3$–$C_7$ substituted cycloalkyl group;

$R^2$ is selected from the group consisting of a $C_1$–$C_{10}$ alkyl, $C_1$–$C_{10}$ substituted alkyl, $C_7$–$C_{16}$ phenylalkyl, $C_7$–$C_{16}$ substituted phenylalkyl, phenyl, substituted phenyl, $C_3$–$C_7$ cycloalkyl, $C_3$–$C_7$ substituted cycloalkyl, and a $C_3$–$C_7$ substituted cycloalkyl group; and $R^3$ is selected from the group consisting of a hydrido, $C_1$–$C_{10}$ alkyl, $C_1$–$C_{10}$ substituted alkyl, $C_2$–$C_{10}$ alkenyl, $C_2$–$C_{10}$ substituted alkenyl, $C_2$–$C_{10}$ alkynyl, $C_2$–$C_{10}$ substituted alkynyl, $C_3$–$C_7$ cycloalkyl, $C_3$–$C_7$ substituted cycloalkyl, phenyl, $C_7$–$C_{16}$ phenylalkyl, $C_7$–$C_{16}$ phenylalkenyl, $C_7$–$C_{16}$ phenylalkenyl and a $C_7$–$C_{16}$ substituted phenylalkenyl group.

In a particularly preferred embodiment, an $R^1$ group is a side chain from an amino acid other than cysteine and proline. Such a preferred $R^1$ group is selected from the group consisting of Ala, Phe, Gly, Asp, Asn, Glu, Gln, His, Ile, Lys, Leu, Met, Arg, Nva (norvaline), Ser, Thr, Val, Trp, Tyr, Nle (norleucine), Cha (clclohexylalanine), Chg (cyclohexylglycine), Fph (4-fluorophenylalanine), Cph (4-chlorophenylalanine), Nph (4-nitrophenylalanine), Aib (2-aminoisobutyric acid), Abu (2-aminobutyric acid), ala, phe, asp, asn, glu, gln, his, ile, lys, leu, met, arg, ser, thr, val, trp, tyr, nle, nva, cha, chg, fph, cph, aib, and abu wherein amino acids written with an initial capital letter are L-amino acids and those written in all lower case letters are D-amino acids. Particularly preferred side chains are those of the above-listed L-amino acids.

An $R^1$ substituent group comprised of an above amino acid side chain or a related amino acid is selected from the group consisting of a hydrido, methyl, benzyl, 2-butyl, N,N-dimethylaminobutyl, N-methylaminobutyl, N-methyl-N-benzylaminobutyl, 2-methylpropyl, methylsulfinylethyl, methylthioethyl, N,N-dimethylaminoethyl, N,N-dimethylaminopropyl, N',N',N'-trimethylguanidinopropyl, N',N',N'-tribenzyl-guanidinopropyl, N',N'-dibenzylguanidinopropyl, N'-methylguanidinopropyl, hydroxymethyl, 1-hydroxyethyl, 2-propyl, N-methyl-3-indolylmethyl, 4-methoxybenzyl, 4-hydroxybenzyl, propyl, butyl, cyclohexylmethyl, phenyl, 2-naphthylmethyl, and a 4-imidazolylmethyl substituent.

In the above Formula I, the stereochemistry of the chiral $R^1$ group can independently be in the R or S configuration, or a mixture of the two. For instance, as noted above, the $R^1$ group can be the side chain substituent of various amino acids that can be in the L- or D-configuration. As a consequence of an $R^1$ substituent being in one or both of two stereoconfigurations, the $R^1$ group is usually illustrated bonded to the triazinetrione ring by a straight line. However, a contemplated single compound or the compounds of a library can have a chiral structure corresponding to one or the other of Formulas IIA (2R) or IIB (2S) shown below,

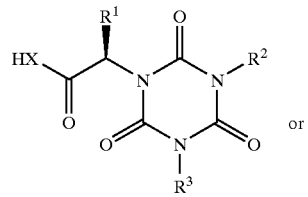

IIA or

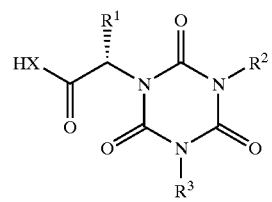

IIB wherein a darkened, wedge-shaped line indicates a bond extending upwardly from the plane of the page and a dashed, wedge-shaped line indicates a bond extending downwardly below the plane of the page.

In a preferred method of synthesis and therefore in a preferred compound of Formulas I or II or a library of such compounds, an $R^2$-containing isocyanate ($R^2$CNO) is reacted with the free amine of a solid phase-bound amino acid residue. Illustrative $R^2$ isocyanate compounds that provide $R^2$ substituent groups to a contemplated compound or library of compounds include aliphatic isocyanates such as methyl isocyanate, ethyl isocyanate, isopropyl isocyanate, n-propyl isocyanate, butyl isocyanate, t-butyl isocyanate, cyclohexyl isocyanate, n-octadecyl isocyanate, and aromatic isocyanates such as phenyl isocyanate, benzyl isocyanate, 2-fluorophenyl isocyanate, 3-fluorophenyl isocyanate, 4-fluorophenyl isocyanate, 2-chlorophenyl isocyanate, 3-chlorophenyl isocyanate, 4-chlorophenyl isocyanate, 2-bromophenyl isocyanate, 3-bromophenyl isocyanate, 4-bromophenyl isocyanate, 3-chloro-4-methylphenyl isocyanate, 3-bromo-4-methylphenyl isocyanate, 3-fluorosulfonyl-phenyl isocyanate, 3,4-(methylenedioxy) phenyl isocyanate, 4-phenoxyphenyl isocyanate, trans-2-phenylcyclopropyl isocyanate, 4-toluenesulfonyl isocyanate, 2-tolyl isocyanate, 3-tolyl isocyanate, 4-tolyl isocyanate, 2-methoxyphenyl isocyanate, 3-methoxyphenyl isocyanate, 4-methoxyphenyl isocyanate, α,α,α-trifluoro-2-tolyl isocyanate, α,α,α-trifluoro-3-tolyl isocyanate, α,α,α-trifluoro-4-tolyl isocyanate, 2,5-dimethylphenyl isocyanate, 3,4-dimethylphenyl isocyanate and 3,5-dimethylphenyl isocyanate. A more comprehensive list of useful $R^2$ isocyanate compounds can be found at http://www.aldrich.sial.com under the listings "Aldrich", "organics" and "isocyanates & isothiocyanates"; the monoisocyanate compounds listed therein are incorporated by reference. Particularly preferred $R^2$ substituents are phenyl, benzyl, 2-, 3- and 4-methoxyphenyl, 4-halophenyl, 2-, 3- and 4-tolyl, 4-ethylphenyl, 3,4-(methylenedioxy)phenyl, 4-phenoxyphenyl, α,α,α-trifluoro-p-tolyl, 2,5-dimethylphenyl and $C_1$–$C_6$ alkyl.

An $R^3$ substituent other than hydrido typically arises in a contemplated triazinetrione via an alkylation reaction of the 5-position nitrogen atom by an alkylating agent that is typically designated $R^3X$, where X is a leaving group such as a halide, toluenesulfonate or methanesulfonate or the like as are well-known in the art. An $R^3$ substituent is selected from the group consisting of a $C_1$–$C_{10}$ alkyl, $C_2$–$C_{10}$ alkenyl, benzyl, substituted benzyl, naphthyl, or substituted naphthyl group. Preferably, $R^3$ is a $C_1$–$C_6$ alkyl, $C_2$–$C_6$ alkenyl, benzyl, or substituted benzyl group.

A $R^3$ substituent is more preferably a methyl, ethyl, allyl, benzyl or substituted benzyl group where the benzyl substituent is a halogen (fluoro, chloro, bromo or iodo), a $C_1$–$C_6$ alkyl, a $C_1$–$C_6$ alkoxy, a trifluoromethyl or a trifluoromethoxy group. In addition to hydrido, illustrative particularly preferred $R^3$ substituents are selected from the group consisting of a methyl, benzyl, 2-, 3- and 4-methylbenzyl, 2-, 3- and 4-fluorobenzyl, 2-, 3- and 4-chlorobenzyl, 2,4-, 3,4-, 3,5- and 2,6-difluorobenzyl, 4-(trifluoromethyl)benzyl, 4-(trifluoromethoxy)benzyl, 2-, 3-, and 4-methoxybenzyl, 3,5- and 3,4-dimethoxybenzyl, 2-, 3- and 4-nitrobenzyl, 2-, 3- and a 4-phenylbenzyl substituent.

One or more of the triazinetrione compounds of Formulas I or II can be present as a pharmaceutically-acceptable salt. The term "pharmaceutically-acceptable salt" encompasses those salts that form with the carboxylate anions or ammonium cations and include salts formed with the organic and inorganic cations and anions discussed below. Furthermore, the term includes salts that form by standard acid-base reactions with basic groups (such as amino groups) and organic or inorganic acids. Such acids include hydrochloric, sulfuric, phosphoric, acetic, succinic, citric lactic, maleic, fumaric, palmitic, cholic, pamoic, mucic, D-glutamic, d-camphoric, glutaric, phthalic, tartaric, lauricc, stearic, salicyclic, methanesulfonic, benzenesulfonic, sorbic, picric, benzoic, cinnamic, and like acids.

The term "organic or inorganic cation" refers to counterions for the carboxylate anion of a carboxylate salt. The counter-ions are chosen from the alkali and alkaline earth metals, (such as lithium, sodium, potassium, barium and calcium): ammonium; and the organic cations such as (dibenzylammonium, benzylammonium, 2-hydroxymethyl-ammonium, bis(2-hydroxyethyl)ammonium, phenylethylbenzyl ammonium, dibebenzylethylenediammoniurn, and like cations). Other cations encompassed by the above term include the protonated form of procaine, quinine and N-methylglucosamine, and the protonated forms of basic amino acids such as glycine, ornithine, histidine, phenylglycine, lysine and arginine. Furthermore, any zwitterionic form of the instant compounds formed by a carboxylic acid and an amino group is referred to by this term. A preferred cation for the carboxylate anion is the sodium cation.

A compound of Formula I can also be present as a solvate and hydrate. Thus, these compounds can crystallize with, for example, waters of hydration, or one, a number of, or any fraction thereof of molecules of the mother liquor solvent. The solvates and hydrates of such compounds are included within the scope of this invention.

In any of the Formulas herein, the term "$C_1$–$C_{10}$ alkyl" denotes a straight or branched chain radical such as a methyl, ethyl, n-propyl, isopropyl, n-butyl, sec-butyl, tert-butyl, amyl, tert-amyl, hexyl, heptyl, decyl group and the like. The term "lower alkyl" denotes a $C_1$–$C_6$ alkyl group. A preferred "$C_1$–$C_{10}$ alkyl" group is a methyl group.

The term "$C_2$–$C_{10}$ alkenyl" denotes a radical such as a vinyl, allyl, 2-butenyl, 3-butenyl, 2-pentenyl, 3-pentenyl, 4-pentenyl, 2-hexenyl, 3-hexenyl, 4-hexenyl, 5-hexenyl, 2-heptenyl, 3-heptenyl, 4-heptenyl, 5-heptenyl, 6-heptenyl and a 2-decenyl group and the like, as well as dienes and trienes of straight and branched chains containing up to ten carbon atoms and at least one carbon-to-carbon (ethylenic) double bond.

The term "$C_2$–$C_{10}$ alkynyl" denotes a radical such as ethynyl, propynyl, butynyl, pentynyl, hexynyl, heptynyl, decynyl and the like, as well as di- and triynes of straight and branched chains containing up to ten carbon atoms and at least one carbon-to-carbon (acetylenic) triple bond.

The term "$C_1$–$C_{10}$ substituted alkyl", "$C_2$–$C_{10}$ substituted alkenyl" and "$C_2$–$C_{10}$ substituted alkeynyl" denote that the above $C_1$–$C_{10}$ alkyl group and $C_2$–$C_{10}$ alkenyl and alkynyl groups are substituted by one or more, and preferably one or two, halogen, hydroxy, protected hydroxy, $C_3$–$C_7$ cycloalkyl, $C_3$–$C_7$ substituted cycloalkyl, naphthyl, substituted naphthyl, adamantyl, abietyl, thiofuranyl, indolyl, substituted indolyl, amino, protected amino, (monosubstituted) amino, protected (monosubstituted) amino, (disubstituted) amino, guanidino, (monosubstituted)guanidino, (disubstituted)guanidino, (trisubstituted)guanidino, imidazolyl pyrolidinyl, $C_1$–$C_7$ acyloxy, nitro, heterocycle, substituted heterocycle, $C_1$–$C_4$ alkyl ester, carboxy, protected carboxy, carbamoyl, carbamoyloxy, carboxamide, protected carboxamide, cyano, methylsulfonylamino, methylsulfonyl, sulfhydryl, $C_1$–$C_4$ alkylthio, $C_1$–$C_4$ alkyl sulfonyl or $C_1$–$C_4$ alkoxy groups. The substituted alkyl groups can be substituted once or more, and preferably once or twice, with the same or with different substituents.

Examples of the above substituted alkyl groups include the cyanomethyl, nitromethyl, chloromethyl, hydroxymethyl, tetrahydropyranyloxymethyl, trityloxymethyl, propionyloxymethyl, aminomethyl, carboxymethyl, allyloxycarbonylmethyl, allylcarbonylaminomethyl, carbamoyloxymethyl, methoxymethyl, ethoxymethyl, t-butoxymethyl, acetoxymethyl, chloromethyl, bromomethyl, iodomethyl, 6-hydroxy-hexyl, 2,4-dichloro(n-butyl), 2-amino(isopropyl), 2-carbamoyloxyethyl chloroethyl, bromoethyl, fluoroethyl, iodoethyl, chloropropyl, bromopropyl, fluoropropyl, iodopropyl and the like.

In preferred embodiments of the subject invention, $C_1$–$C_{10}$ alkyl, $C_2$–$C_{10}$ alkenyl, $C_2$–$C_{10}$ alkynyl, $C_1$–$C_{10}$ substituted alkyl, $C_2$–$C_{10}$ substituted alkenyl, or $C_2$–$C_{10}$ substituted alkynyl, are more preferably $C_1$–$C_6$ or $C_2$–$C_6$, respectively, as is appropriate for unsaturated substituents. However, it should be appreciated by those of skill in the art that one or a few carbons usually can be added to an alkyl, alkenyl, alkynyl, substituted or unsubstituted, without substantially modifying the structure and function of the subject compounds and that, therefore, such additions would not depart from the spirit of the invention.

The term "$C_1$–$C_4$ alkoxy" as used herein denotes groups that are ether groups containing up to four carbon atoms such as methoxy, ethoxy, n-propoxy, isopropoxy, n-butoxy, t-butoxy and like groups. A preferred $C_1$–$C_4$ alkoxy group is methoxy.

The term "$C_1$–$C_7$ acyloxy" denotes a carboxy group-containing substituent containing up seven carbon atoms such as formyloxy, acetoxy, propanoyloxy, butanoyloxy, pentanoyloxy, hexanoyloxy, heptanoyloxy, benzoyloxy and the like.

Similarly, the term "$C_1$–$C_7$ acyl" encompasses groups such as formyl, acetyl, propionoyl, butyroyl, pentanoyl, hexanoyl, heptanoyl, benzoyl and the like.

The substituent term "$C_3$–$C_7$ cycloalkyl" includes the cyclopropyl, cyclobutyl, cyclopentyl, cyclohexyl or cycloheptyl rings. The substituent term "$C_3$–$C_7$ substituted cycloalkyl" indicates an above cycloalkyl ring substituted by a halogen, hydroxy, protected hydroxy, phenyl, substituted phenyl, heterocycle, substituted heterocycle, $C_1$–$C_{10}$ alkyl, $C_1$–$C_4$ alkoxy, carboxy, protected carboxy, amino, or protected amino.

The substituent term "$C_5$–$C_7$ cycloalkenyl" indicates a substituent that is itself a 1-, 2-, or 3-substituted cyclopentenyl ring, a 1-, 2-, 3- or 4-substituted cyclohexenyl ring or a 1-, 2-, 3-,4- or 5-substituted cycloheptenyl ring, whereas the term "substituted $C_3$–$C_7$ cycloalkenyl" denotes the above $C_3$–$C_7$ cycloalkenyl rings substituted by a $C_1$–$C_{10}$ alkyl radical, halogen, hydroxy, protected hydroxy, $C_1$–$C_4$ alkoxy, carboxy, protected carboxy, amino, or protected amino, The term "heterocyclic ring" or "heterocycle" denotes an optionally substituted 5-membered or 6-membered ring that has 1 to 4 heteroatoms, such as oxygen, sulfur and/or nitrogen, in particular nitrogen either alone or in conjunction with sulfur or oxygen ring atoms. These five-membered or six-membered rings can be fully unsaturated or partially unsaturated, with fully unsaturated rings being preferred.

Preferred heterocyclic rings include pyridino, pyrimidino, and pyrazino, furano, and thiofurano rings. The heterocyles can be substituted or unsubstituted as for example, with such substituents as those described in relation to substituted phenyl or substituted naphthyl.

The term "$C_7$–$C_{16}$ phenylalkyl" or "$C_7$–$C_{16}$ aralkyl" denotes a $C_1$–$C_{10}$ alkyl group substituted at any position by a phenyl ring. Examples of such a group include benzyl, 2-phenylethyl, 3-phenyl(n-prop-1-yl), 4-phenyl(hex-1-yl), 3-phenyl(n-am-2-yl), 3-phenyl(sec-butyl), and the like. A preferred $C_7$–$C_{16}$ phenylalkyl group is the benzyl group.

The term "$C_7$–$C_{16}$ substituted phenylalkyl" denotes an above $C_7$–$C_{16}$ phenylalkyl group substituted on the $C_1$–$C_{10}$ alkyl portion with one or more, and preferably one or two, groups selected from the group consisting of a halogen, hydroxy, protected hydroxy, keto, $C_2$–$C_3$ cyclic ketal phenyl, amino, protected amino, $C_1$–$C_7$ acyloxy, nitro, carboxy, protected carboxy, carbamoyl, carbarnoyloxy, cyano, N-(methylsulfonylamino) or $C_1$–$C_4$ alkoxy group, whose phenyl group portion can be substituted with 1 or 2 groups selected from the group consisting of a halogen, hydroxy, protected hydroxy, nitro, $C_1$–$C_{10}$ alkyl, $C_1$–$C_6$ substituted alkyl, $C_1$–$C_4$ alkoxy, carboxy, protected carboxy, carboxymethyl, protected carboxymethyl, hydroxymethyl, protected hydroxymethyl, aminomethyl, protected aminomethyl, amino, (monosubstituted)amino, (disubstituted)amino, a N-(methylsulfonylamino) group, or a phenyl group that is itself substituted or unsubstituted. When either the $C_1$–$C_{10}$ alkyl portion or the phenyl portion or both are mono- or di-substituted, the substituents can be the same or different.

Examples of "$C_7$–$C_{16}$ substituted phenylalkyl" include groups such as 2-phenyl-1-chloroethyl, 2-(4-methoxyphenyl)eth-1-yl, 2,6-dihydroxy-4-phenyl(n-hex-2-yl), 5-cyano-3-methoxy-2-phenyl(n-pent-3-yl), 3-(2,6-dimethylphenyl)n-prop-1-yl, 4-chloro-3-aminobenzyl, 6-(4-methoxyphenyl)-3-carboxy(n-hex-1-yl), 5-(4-aminomethylphenyl)-3-(aminomethyl)(n-pent-2-yl), 5-phenyl-3-keto-(n-pent-1-yl), 4-(4-aminophenyl)-4-(I.4-oxetanyl)(n-but-1-yl), and the like.

The term "$C_7$–$C_{16}$ phenylalkenyl" denotes a $C_1$–$C_{10}$ alkenyl group substituted at any position by a phenyl ring. The term "$C_7$–$C_{16}$ substituted phenylalkenyl" denotes a $C_7$–$C_{16}$ arylalkenyl group substituted on the $C_1$–$C_{10}$ alkenyl portion. Substituents can the same as those as defined above in relation to $C_7$–$C_{16}$ phenylalkyl and $C_7$–$C_{16}$ substituted phenylalkyl. A preferred $C_7$–$C_{16}$ substituted phenylalkenyl is 3-(4-nitrophenyl)-2-propenyl.

The term "substituted phenyl" specifies a phenyl group substituted at one or more positions, preferably at one or two positions, with moieties selected from the group consisting of halogen, hydroxy, protected hydroxy, cyano, nitro, $C_1$–$C_{10}$ alkyl, $C_1$–$C_{10}$ substituted alkyl, $C_1$–$C_4$ alkoxy, carboxy, protected carboxy, carboxymethyl, protected carboxymethyl, hydroxymethyl, protected hydroxymethyl, amino, protected anlino, (monosubstituted)amino, protected (monosubstituted) amino, (disubstituted)amino, trifluoromethyl, N-(methylsulfonylamino), or phenyl that is itself substituted or unsubstituted such that, for example, a biphenyl group results.

Illustrative substituents embraced by the term "substituted phenyl" include a mono- or di(halo)phenyl group such as 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl and the like; a mono or di(hydroxy)phenyl groups such as 4-hydroxyphenyl, 3-hydroxyphenyl, 2,4-dihydroxyphenyl, the protected hydroxy derivatives thereof and the like; a nitrophenyl group such as 3- or 4-nitrophenyl, a cyanophenyl group for example, 4-cyanophenyl; a mono- or di(lower alkyl)phenyl group such as 4-methylphenyl, 2,4-dimethylphenyl, 2-methylphenyl, 4-(isopropyl)phenyl, 4-ethylphenyl, 3-(n-prop-1-yl)phenyl and the like: a mono or di(alkoxyl)phenyl group for example, 2,6-dimethoxyphenyl, 4-methoxyphenyl, 3-ethoxyphenyl, 4-(isopropoxy)phenyl, 4-(t-butoxy)phenyl, 3-ethoxy-4-methoxyphenyl, 3-(4-methylphenoxy)phenyl, and the like; 3- or 4-trifluoromethylphenyl; a mono- or dicarboxyphenyl or (protected carboxy)phenyl group such as 4-carboxyphenyl or 2,4-di(protected carboxy)phenyl; a mono- or di(hydroxymethyl)phenyl or (protected hydroxymethyl) phenyl such as 3-(protected hydroxymethyl)phenyl or 3,4-di(hydroxymethyl)phenyl; a mono- or di(aminomethyl) phenyl or (protected aminomethyl)phenyl such as 2-(aminomethyl)phenyl or 2,4-(protected aminomethyl) phenyl; or a mono- or di(N-(methylsulfonylamino))phenyl such as 3-(N-(methylsulfonylamino))phenyl. Also, the term "substituted phenyl" represents disubstituted phenyl groups wherein the substituents are different. For example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl and the like are contemplated.

The term "substituted naphthyl" specifies a naphthyl group substituted with one or more, and preferably one or two moieties selected from the group consisting of a halogen, hydroxy, protected hydroxy, cyano, nitro, $C_1$–$C_{10}$ alkyl, $C_1$–$C_4$ alkoxy, carboxy, protected carboxy, carboxymethyl, protected carboxymethyl, hydroxymethyl, protected hydroxymethyl, amino, protected amino, (monosubstituted) amino, protected (monosubsticuted) amino, (disubstituted) amino trifluoromethyl, or a N-(methylsulfonylamino) group. Examples of substituted naphthyl include 2-(methoxy)naphthyl and 4-(methoxy) naphthyl.

The term "substituted indolyl" specifies a indolyl group substituted, either at the nitrogen or carbon, or both, with one or more, and preferably one or two, moieties selected from the group consisting of a halogen, hydroxy, protected hydroxy, cyano, nitro, $C_1$–$C_{10}$ alkyl, $C_1$–$C_{10}$ substituted alkyl, $C_1$–$C_{10}$ alkenyl, $C_7$–$C_{16}$ phenylalkyl, $C_7$–$C_{16}$ substituted phenylalkyl, $C_1$–$C_6$ alkoxy, carboxy, protected carboxy, carboxymethyl, protected carboxymethyl, hydroxymethyl, protected hydroxymethyl, amino, protected amino, monosubstituted amino, or a disubstituted amino group.

Examples of the term "substituted indolyl" includes such groups as 6-fluoro, 5-fluoro, 5-bromo, 5-hydroxy, 5-methyl, 6-methyl, 7-methyl, 1-methyl, 1-ethyl, 1-benzyl, 1-napthylmethyl, and the like. An example of a disubstituted indolyl is 1-methyl-5-methyl indolyl.

The terms "halo" and "halogen" refer to the fluoro, chloro, bromo, or iodo groups.

The term "(monosubstituted)amino" refers to an amino group with one substituent selected from the group consisting of phenyl, substituted phenyl, $C_1$–$C_{10}$ alkyl, and $C_7$–$C_{16}$ arylalkyl, wherein the latter three substituent terms are as defined above. The (monosubstituted)amino can additionally have an amino-protecting group as encompassed by the term "protected (monosubstituted)amino."

The term "(disubstituted)amino" refers to amino groups with two substituents selected from the group consisting of phenyl, substituted phenyl, $C_1$–$C_{10}$ alkyl, and $C_7$–$C_{16}$ arylalkyl wherein the latter three substituent terms are as described above. The two substituents can be the same or different.

The terms "(monosubstituted)guanidino", "(disubstituted)guanidino." and "(trisubstituted)guanidino" are used to mean that a guanidino group is substituted with one, two, or three substituents, respectively. The substituents can be any of those as defined above in relation to (monosubstituted)amino and (disubstituted)amino and, where more than one substituent is present, the substituents can be the same or different.

The term "amino-protecting group" as used herein refers to one or more selectively removable substituents on the amino group commonly employed to block or protect the amino functionality. The term "protected (monosubstituted) amino" means there is an amino-protecting group on the monosubstitutedamino nitrogen atom. In addition, the term "protected carboxamide" means there is an amino-protecting group present replacing the proton of the amido nitrogen so that di-N-alkylation.

Examples of such amino-protecting groups include the formyl ("For") group, the trityl group (Trt), the phthalimido group, the trichloroacetyl group, the chloroacetyl, bromoacetyl, and iodoacetyl groups. Urethane blocking groups, such as t-butoxy-carbonyl ("Boc"), 2-(4-biphenylyl) propyl(2)-oxycarbonyl ("Bpoc"), 2-phenylpropyl(2) oxycarbonyl ("Poc"), 2-(4-xenyl)-isopropoxycarbonyl, 1,1-diphenylethyl(1)oxycarbonyl, 1,1-diphenylpropyl(1) oxycarbonyl, 2-(3,5-dimethoxyphenyl)propyl(2) oxycarbonyl ("Ddz"), 2-(p-5-toluyl)propyl-(2)oxycarbonyl, cyclo-pentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)ethoxycarbonyl, 2-(methylsulfonyl) ethoxycarbonyl, 2-(triphenylphosphino)ethoxycarbonyl, 9-fluoroenylmethoxycarbonyl ("Fmoc"), 2-(trimethylsilyl) ethoxycarbonyl, allyloxycarbonyl, 1-(trimethylsilylmethyl) prop-1-enyloxycarbonyl, 5-benz-isoxalylmethoxycarbonyl, 4-acetoxybenzyloxycarbonyl, 2,2,2-trichloroethoxycarbonyl, 2-ethynyl(2)propoxycarbonyl, cyclopropylmethoxycarbonyl, isobornyloxycarbonyl, 1-piperidyloxycarbonyl, benzyloxycarbonyl ("Z"), 4-phenylbenzyloxycarbonyl, 2-methylbenzyloxycarbonyl, 2,4,5,-tetramethylbenzyloxycarbonyl ("Tmz"), 4-methoxybenzyl-oxycarbonyl, 4-fluorobenzyloxycarbonyl, 4-chloro-benzyloxycarbonyl, 3-chlorobenzyloxycarbonyl, 2-chlorobenzyloxycarbonyl, dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 4-(decyloxy)benzyloxycarbonyl, and the like, the benzoylmethylsulfonyl group, dithiasuccinoyl ("Dts') group, the 2-(nitro)phenylsulfenyl group ("Nps'), the diphenylphosphine oxide group, and like amino-protecting groups. The species of amino-protecting group employed is usually not critical so long as the derivatized amino group is stable to the conditions of the subsequent reactions and can be removed at the appropriate point without disrupting the remainder of the compound. Preferred amino-protecting groups are Boc and Fmoc.

Further examples of amino-protecting groups embraced by the above term are well known in organic synthesis and the peptide art and are described by, for example T. W. Greene and P. G. M. Wuts, *Protective Groups in Organic Synthesis*, $2^{nd}$ ed., John Wiley and Sons, New York, Chapter 7, 1991; M. Bodanzsky, *Principles of Peptide Synthesis*, $1^{st}$ and $2^{nd}$ revised eds., Springer-Verlag, New York, 1984 and 1993; and Stewart and Young, *Solid Phase Peptide Synthesis*, $2^{nd}$ ed., Pierce Chemical Co, Rockford. Ill. 1984.

The related term "protected amino" defines an amino group substituted with an amino-protecting group discussed above.

The term "carboxy-protecting group" as used herein refers to one of the ester derivatives of the carboxylic acid group commonly employed to block or protect the carboxylic acid group while reactions are carried out on other functional groups on the compound. Examples of such carboxylic acid protecting groups include 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-methoxytrityl, 4,4',4"-trimethoxytrityl, 2-phenylprop-2-yl, trimethylsilyl, t-butyldimethylsilyl, 2,2,2-trichloroethyl, β-(trimethylsilyl) ethyl, β-[di(n-butyl)methylsilyl]ethyl, p-toluenesulfonylethyl, 4-nitrobenzyl-sulfonylethyl, allyl, cinnamyl, 1-(trimethylsilylmethyl)-prop-1-en-3-yl, and like moieties. The species of carboxy-protecting group employed is also usually not critical so long as the derivatized carboxylic acid is stable to the conditions of subsequent reactions and can be removed at the appropriate point without disrupting the remainder of the molecule.

Further examples of these groups are found in E. Haslam, *Protective Groups in Organic Chemistry*, J. G. W. McOmie Ed., Plenum Press, New York 1973, Chapter 5 and T. W. Greene and P. G. M. Wuts, *Protective Groups in Organic Synthesis* $2^{nd}$ ed., John Wiley and Sons, New York, 1991, Chapter 5, each of which is incorporated herein by reference. A related term is "protected-carboxy", which refers to a carboxy group substituted with one of the above carboxy-protecting groups.

The term "hydroxy-protecting group" refers to readily cleavable groups bonded to hydroxyl groups, such as the tetrahydropyranyl, 2-methoxyprop-2-yl, 1-ethoxyeth-1-yl, methoxymethyl, β-methoxyethoxymethyl, methylthiomethyl, t-butyl, t-amyl, trityl, 4-methoxytrityl, 4,4'-dimethoxytrityl, 4,4',4"-trimethoxytrityl, benzyl, allyl, trimethylsilyl, (t-butyl)dimethylsilyl and 2,2,2-trichloroethoxycarbonyl groups, and the like. The species of hydroxy-protecting groups is also usually not critical so long as the derivatized hydroxyl group is stable to the conditions of subsequent reaction(s) and can be removed at the appropriate point without disrupting the remainder of the compound.

Further examples of hydroxy-protecting groups are described by C. B. Reese and E Haslam, *Protective Groups in Organic Chemistry*, J. G. W. McOmie, Ed., Plentun Press, New York 1973, Chapters 3 and 4, respectively, and T. W. Greene and P. G. M. Wuts, *Protective Groups in Organic Synthesis*, $2^{nd}$ ed., John Wiley and Sons, New York, 1991, Chapters 2 and 3, whose disclosures are also incorporated by reference.

The substituent term "$C_1$-$C_4$ alkylthio" refers to sulfide groups such as methylthio, ethylthio, n-propylthio, isopropylthio, α-butylthio, t-butylthio and like groups.

The substituent term "$C_1$-$C_4$ alkylsulfoxide" indicates sulfoxide groups such as methylsulfoxide, ethylsulfoxide, α-propylsulfoxide, iso-propyl-sulfoxide, n-butylsulfoxide, sec-butylsulfoxide, and the like.

The term "$C_1$-$C_4$ alkylsulfonyl", encompasses groups such as methylsulfonyl, ethylsulfonyl, n-propylsulfonyl, isopropylsulfonyl, -butylsulfonyl, t-butylsulfonyl, and the like.

Phenylthio, phenyl sulfoxide, and phenylsulfonyl compounds are known in the art and these have their art-recognized definitions. By "substituted phenylthio", "substituted phenyl sulfoxide", and "substituted phenylsulfonyl" is meant that the phenyl can be substituted as described above in relation to "substituted phenyl."

The substituent terms "cyclic $C_2$-$C_{10}$ alkylene", "substituted cyclic $C_2$-$C_{10}$ alkylene", "cyclic $C_2$-$C_{10}$ heteroalkylene," and "substituted cyclic $C_2$-$C_{10}$ heteroakylene" defines a cyclic group bonded ("fused") to the phenyl radical. The cyclic group can be saturated or contain one or two double bonds. Furthermore, the cyclic group can have one or two methylene groups replaced by one or two oxygen, nitrogen or sulfur atoms.

The cyclic alkylene or heteroalkylene group can be substituted once or twice by substituents selected from the group consisting of hydroxy, protected-hydroxy, carboxy, protected-carboxy, keto, ketal, $C_1$-$C_4$ alkoxycarbonyl, $C_1$-$C_4$ alkanoyl, $C_1$-$C_{10}$ alkyl, carbamoyl, $C_1$-$C_4$ alkoxy, $C_1$-$C_4$, alkylthio, $C_1$-$C_4$ alkylsulfoxide, $C_1$-$C_4$ alkylsulfonyl, halo, amino, protected-amino, hydroxymethyl and a protected-hydroxymethyl group.

A cyclic alkylene or heteroalkylene group fused onto the benzene radical can contain two to ten ring members, but it preferably contains four to six members. Examples of such saturated cyclic groups include a bicyclic ring system that is a 2,3-dihydroindanyl or a tetralin ring. When the cyclic groups are unsaturated, examples occur when the resultant bicyclic ring system is a naphthyl ring or indanyl.

An example of a cyclic group that can be fused to a phenyl radical that has two oxygen atoms and that is fully saturated is dioxanyl. Examples of fused cyclic groups that each contains one oxygen atom and one or two double bonds occur when the phenyl ring is fused to a furo, pyrano, dihydrofurano or dihydropyrano ring. Cyclic groups that each have one nitrogen atom and contain one or two double more double bonds are illustrated where the phenyl is fused to a pyridino or pyrano ring. An example of a fused ring system having one nitrogen and two phenyl radicals is a carbozyl group. Examples of cyclic groups that each have one sulfur atom and contain one or two double bonds occur where the benzene ring is fused to a thieno, thiopyrano, dihydrothieno, or dihydrothiopyrano ring. Examples of cyclic groups that contain two heteroatoms selected from sulfur and nitrogen and one or two double bonds occur where the phenyl ring is fused to a thiazolo, isothiazolo, dihydrothiazolo or dihydroisothiazolo ring. Examples of cyclic groups that contain two heteroatoms selected from oxygen and nitrogen and one or two double bonds occur where the benzene ring is fused to an oxazole, isoxazole, dihydroxazole or dihydroisoxazole ring. Examples of cyclic groups that contain two nitrogen heteroatoms and one or two double bonds occur where the benzene ring is fused to a pyrazolo, imidazolo, dihydropyrazolo or dihydroimidazolo ring.

Examples of cyclic groups that each have one nitrogen atom and contain one or two double more double bonds occur when the phenyl is fused to a pyridino or pyrano ring. An example of a fused ring system having one nitrogen and two phenyl radicals is a carbozyl group. Examples of cyclic groups that each have one sulfur atom and contain one or two double bonds occur when the phenyl is fused to a thieno, thiopyrano, dihydrothieno, or dihydrothiopyrano ring.

Examples of cyclic groups that contain two heteroatoms selected from sulfur and nitrogen and one or two double bonds occur when the phenyl ring is fused to a thiazolo, isothiazolo, dihydrothiazolo or dihydroisothiazolo ring. Examples of cyclic groups that contain two heteroatoms selected from oxygen and nitrogen and one or two double bonds occur when the benzene ring, is fused to an oxazolo, isoxazolo, dihydroox-azolo or dihydroisoxazolo ring. Examples of cyclic groups that contain two nitrogen heteroatoms and one or two double bonds occur when the benzene ring is fused to a pyrazolo, imidazolo, dihydropyrazolo or dihydroimidazolo ring.

Pharmaceutical Compositions

A contemplated individual compound corresponding to Formulas I or II or a pharmaceutically acceptable salt thereof can be utilized in a pharmaceutical composition. For preparing pharmaceutical compositions containing a compound of the invention or salt thereof, inert, pharmaceutically acceptable carriers are used. The pharmaceutical carrier can be either solid or liquid. Solid form preparations include, for example, powders, tablets, dispersible granules, capsules, cachets, and suppositories. Techniques and materials for preparing pharmaceutical compositions are well-known in the art and will therefore not be dealt with in depth here.

A solid carrier can be one or more substances that can also act as diluents, flavoring agents, solubilizers, lubricants, suspending agents, binders, or tablet disintegrating agents; it can also be an encapsulating material.

In powders, the carrier is generally a finely divided solid that is in a mixture with the finely divided active component. In tablets, the active compound is mixed with the carrier having the necessary binding properties in suitable proportions and compacted in the shape and size desired.

For preparing pharmaceutical composition in the form of suppositories, a low-melting wax such as a mixture of fatty acid glycerides and cocoa butter is first melted and the active ingredient is dispersed therein by, for example, stirring. The molten homogeneous mixture is then poured into convenient-sized molds and allowed to cool and solidify.

Powders and tablets preferably contain between about 5 percent to about 70 percent by weight of the active ingredient. Suitable carriers include, for example, magnesium carbonate, magnesium stearate, talc, lactose, sugar, pectin, dextrin, starch, tragacanth, methyl cellulose, sodium carboxymethyl cellulose, a low-melting wax, cocoa butter and the like.

A pharmaceutical composition can include the formulation of the active compound with encapsulating material as a carrier providing a capsule in which the active component (with or without other carriers) is surrounded by a carrier, which is thus in association with it. In a similar manner, cachets are also included.

Tablets, powders, cachets, and capsules can be used as solid dosage forms suitable for oral administration.

Liquid pharmaceutical compositions include, for example, solutions suitable for oral or parenteral administration, or suspensions, and emulsions suitable for oral administration. Sterile water solutions of the active component or sterile solutions of the active component in solvents comprising water, ethanol, or propylene glycol are examples of liquid compositions suitable for parenteral administration.

Sterile solutions can be prepared by dissolving the active component in the desired solvent system, and then passing the resulting solution through a membrane filter to sterilize it or, alternatively, by dissolving the sterile compound in a previously sterilized solvent under sterile conditions.

Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethyl cellulose, and other suspending agents known to the pharmaceutical formulation art.

Preferably, the pharmaceutical composition is in unit dosage form. In such form, the composition is divided into unit doses containing appropriate quantities of the active urea. The unit dosage form can be a packaged preparation, the package containing discrete quantities of the preparation, for example, packeted tablets, capsules, and powders in vials or ampules. The unit dosage form can also be a capsule, cachet, or tablet itself, or it can be the appropriate number of any of these packaged forms.

Library Syntheses and Use

As used herein, a chemical or combinatorial "library" is an intentionally created collection of a plurality of structurally similar, but different molecules. By "structurally similar", it is meant that the constituent compounds of a library have the same ring structure; i.e., a 1,3,5-triazine-2,4,6-trione, and at least two positions at which substituents are bonded to the nitrogen atoms of the ring structure. It is preferred that the member compounds of the library also have the same substitution pattern of substituent groups; i.e., that the at least two substituents be bonded to the same ring nitrogen positions in each member compound. The molecule members of the library are different in that each member has at least one different substituent group from the other members of the library. A library can contain two to thousands or millions of member compounds.

A particular library can also be comprised of members whose substituent groups are all different from each other. Thus, where the shared 1,3,5-triazine-2,4,6-trione ring structure contains substituent groups at two or three of positions, a library can be prepared in which the member molecules contain different groups at each position of substitution.

Alternatively, a plurality of sub-libraries or sets can also be prepared in which a first set has a first substituent that is held constant for all of the members (is present in all members) of the set, whereas the groups at the other substituent positions are different and constitute a mixture of groups at each substituent position. A second set of that plurality has a second, different, first substituent, and the same mixture of different groups at the other substituent positions. A third set of that plurality has a third, different first substituent, and the same mixture of different groups at the other substituent positions, and so on until one decides to stop making sets with different first substituents. Such set pluralities of structurally similar, but different compounds are also often referred to as libraries of libraries, and are particularly useful in ascertaining which compound or compounds of a library are particularly active in an assay of choice.

A library can be prepared by the synthetic means discussed below or otherwise herein and screened for biological activity in a variety of formats (e.g. libraries of soluble molecules). Libraries of compounds can be attached to a solid phase support such as resin beads, silica chips or other solid supports). The libraries can be screened in any variety of assays, such as those discussed below as well as others useful for assessing the biological activity of triazinetriones. The libraries typically contain at least one active compound and are generally prepared such that the compounds are in approximately equimolar quantities.

The nonsupport-bound library mixtures prepared herein are screened in solution in assays. Deconvolution of highly active mixtures can then be carried out by iterative, or positional scanning methods. These techniques, the iterative approach or the positional scanning approach, can be utilized for finding other active compounds within the libraries of the present invention using assays well known in the art.

The iterative approach is well-known and is set forth in general in Houghten et al., *Nature,* 354, 84–86 (1991) and Dooley et al., *Science,* 266, 2019–2022 (1994), both of which are incorporated herein by reference. In the iterative approach, for example, sub-libraries of triazinetriones having three variable N-bonded substituent groups are made wherein the one variable substituent is defined (known and held constant) within the sub-library and the other two N-substituted positions substituents contain mixtures of substituents. An illustrative synthesis a set of such sub-libraries is discussed hereinbelow after the discussion accompanying Scheme 2.

The positional-scanning approach has been described for various libraries as described, for example, in R. Houghten et al. PCT/US91/08694 and U.S. Pat. No. 5,556,762, both of which are incorporated herein by reference. The positional scanning approach is used as described below in the preparation and screening of the libraries.

In the positional scanning approach, sub-libraries are made defining only one variable substituent with each set of sub-libraries and possible sub-libraries with each single variable substituent defined (and all other possibilities at all of the other variable positions) are made and assayed. From the present description one skilled in the art can synthesize libraries wherein two fixed substituent positions are defined at a time. From the assaying of each single-variable defined library, the one or more optimum substituents at that position is determined, pointing to the optimum or at least a series of compounds having a maximum of the desired biological activity. Thus, the number of sub-libraries for compounds with a single substituent position defined is the number of different substituents desired at that position, and the number of all the compounds in each sub-library is the product of the number of substituents at each of the other variables.

Results and Discussion

A. 1,3-Disubstituted-1,3,5-triazine-2,4,6-trione from p-Methylbenzhydrylamine (MBHA) Resin The parallel solid-phase synthesis of 1,3-disubstituted-1,3,5-triazine-2,4,6-triones was carried out on the solid-phase using the "tea-bag" methodology [Houghten, *Proc. Natl. Acad. Sci. U.S.A.* 1985, 82, 5131; U.S. Pat. No. 4,631,211]. To demonstrate the general feasibility of the cyclization, it was initially decided to alkylate the amide nitrogen of the linkage, and then build the triazinetrione moiety on the support by reaction of chlorocarbonyl isocyanate with resin-bound urea Compound 3. The reaction sequence is illustrated in Scheme 1, below.

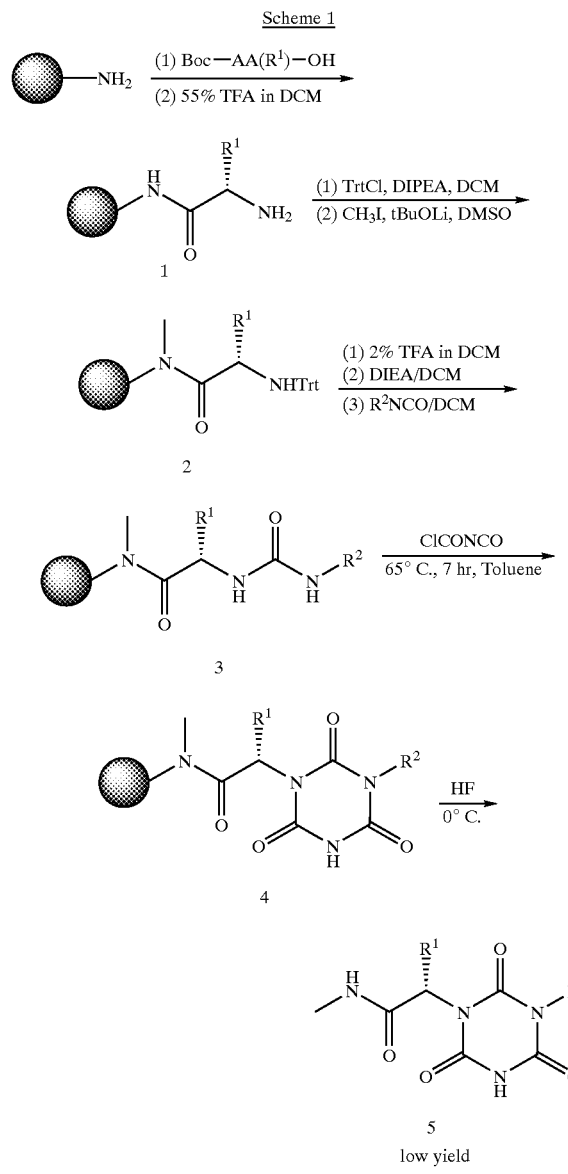

Thus, Boc-protected amino acid [Boc-AA($R^1$)] was attached to the p-methylbenzhydrylamine (MBHA) resin (shown as a circular shaded object in the Scheme) using 1-hydroxybenzotriazole (HOBT) and N,N-diisopropylcarbodiimide (DIC) as coupling reagents in N,N-dimethylformamide (DMF) to form resin-bound N-tert-butyloxycarbonyl (Boc) amino acid Compound 1.

The Boc group was removed using 55% trifluoroacetic acid (TFA) in dichloromethane (DCM). The resulting amine salt was neutralized, and the primary amine was then protected with triphenylmethyl chloride (TrtCl). The secondary amide was then selectively methylated in the presence of lithium t-butoxide and methyl iodide [Nefzi et al., *Tetrahedron.* 1999, 55, 335] to form the N-alkylated resin-bound peptide Compound 2. Upon removal of the trityl group with 2% TFA in dichloromethane (DCM), the N-alkylated resin-bound peptide was neutralized and then reacted with isocyanate to yield resin-bound urea Compound 3. The resin-bound 1,3-disubstituted-1,3,5-triazine-2,4,6-trione Compound 4 was obtained following the treatment of the resin-bound urea Compound 3 with chlorocarbonylisocyanate.

A variety of conditions were studied in order to optimize the cyclization. The conversion of Compound 3 to Compound 4 was completed using chlorocarbonylisocyanate (6 equivalents 0.1M) in toluene at 65° C. for 7 hours. Product Compound 5 was obtained following cleavage from the resin by using HF. Unfortunately, the yield of crude product was low (<15%). The alkylation of the amide nitrogen of the resin linkage appears to increases the acid sensitivity. [Nefzi et al., *Tetrahedron.* 1999, 55, 335.] Presumably, the lower yield was caused by premature cleavage during the cyclization reaction due to the generation of HCl.

To overcome this yield problem, the reaction of chlorocarbonylisocyanate with a non-alkylated resin-bound urea was investigated. On the basis of the above results, it was reasoned that any byproduct formed with the amide group of the linker, which would increase the acidic sensitivity, would be easily cleaved from the resin during the cyclization reaction. The resin-bound triazinetrione would then yield the desired products in good purity after HF cleavage. This synthesis procedure is shown in Scheme 2, below.

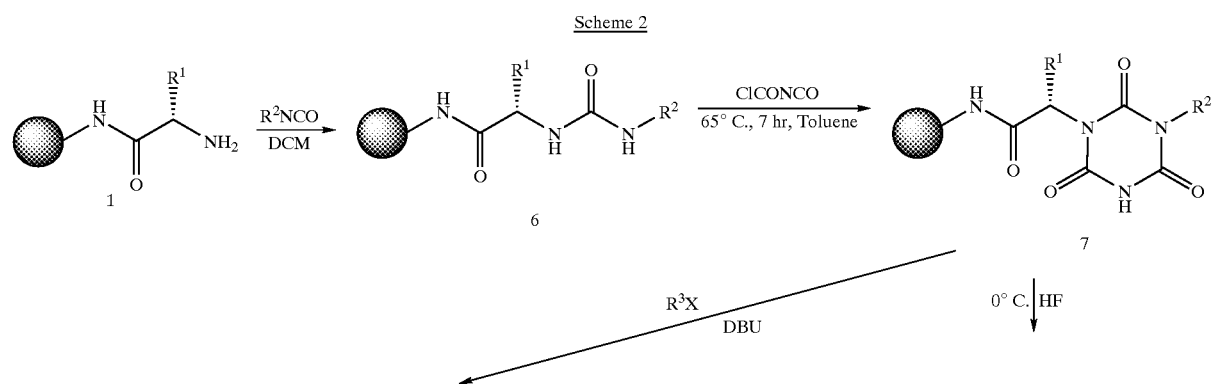

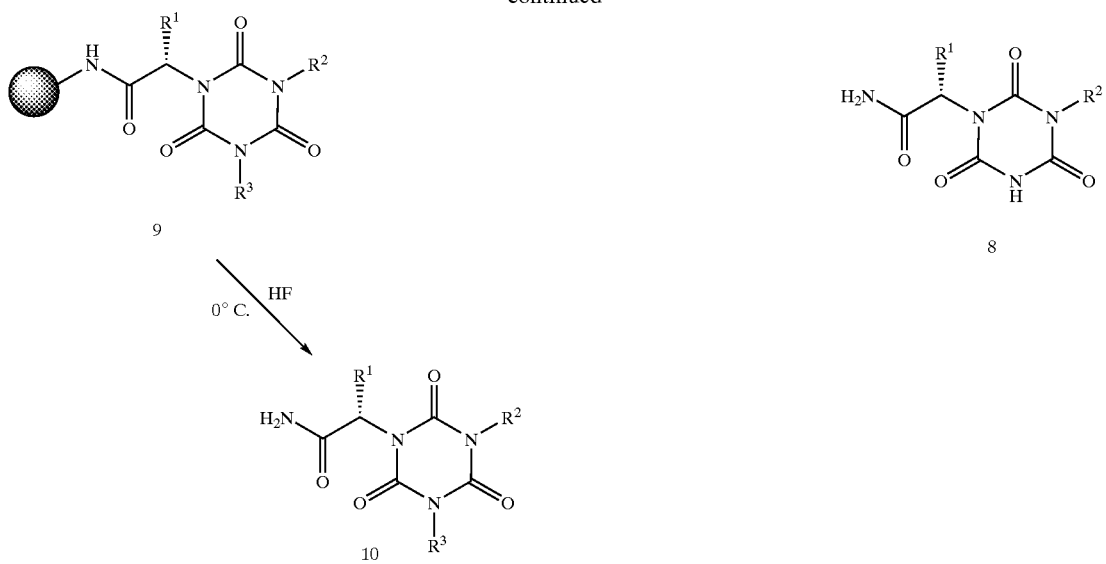

As outlined in Scheme 2, the primary amine of Compound 1 was reacted with an isocyanate in DCM for 3 hours at room temperature to provide the resin-bound urea Compound 6. The reaction was conveniently monitored via the ninhydrin test [Kaiser et al., *Anal. Biochem.* 1970, 34, 595.]. The resin-bound urea Compound 6 was reacted with chlorocarbonylisocyanate in toluene at 65° C. for 7 hours to yield the resin-bound 1,3-disubstituted-1,3,5-triazine-2,4,6-trione, Compound 7. The desired product, Compound 8, was cleaved from the resin using HF for 1.5 hours at 0° C. in moderate yield and good purity. The products were characterized by electrospray LC-MS under ESI conditions, $^1$H and $^{13}$C-NMR.

B. Selective Alkylation at the N-5 Position of the Resin-Bound 1,3-disubstituted-1,3,5-triazine-2,4,6-triones Selective alkylation at the N-5 position of the resin-bound 1,3-disubstituted-1,3,5-triazine-2,4,6-triones, Compounds 7, produced the possibility of alkylation of the linker amide group and O-alkylation. The reaction of Compound 7 with alcohols was first examined under Mitsunobu conditions [(a) Gopalsamy et al., *J. Comb. Chem.* 2001, 3, 278; and (b) Thomas et al., *Tetrahedron Lett.* 1995, 36, 3728]. However, the purity of product Compound 10 was only between 40% to 60%. Starting materials as well as some by-products were observed in the LC-MS.

The reaction of Compound 7 with alkyl halides and a range of bases was thereafter examined. When Bu$^t$OLi, Bu$^t$OK, NaH or NaOMe were used as the base, the N-5 alkylation product Compound 9, as well as dialkylation by-products were found as determined by LC-MS. Selective alkylation at the N-5 position of Compound 7 was accomplished by treatment with alkyl halides in the presence of 1,8-diazabicyclo[5.4.0]-undec-7-ene (DBU). The desired product Compounds 10 were cleaved from the resin using HF for 1.5 hours at 0° C. in good purity. The results are listed in Table 1, below.

TABLE 1

Individual 1,3-disubstituted and 1,3,5-trisubstituted - 1,3,5-triazine-2,4,6-trione Compounds 8,10 from p-methylbenzhydrylamine MBHA Resin

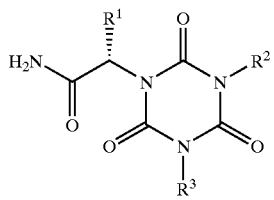

| Product | R$^1$ | R$^2$ | R$^3$ | Yield$^a$ | Purity$^b$ | MW(found)$^c$ ([M + H]$^+$) |
|---|---|---|---|---|---|---|
| 8a | C$_6$H$_5$CH$_2$ | C$_6$H$_5$ | H | 72 | 83 | 352.9 |
| 8b | C$_6$H$_5$CH$_2$ | p-Cl-C$_6$H$_4$ | H | 68 | 81 | 387.5 |
| 8c | C$_6$H$_5$CH$_2$ | p-CH$_3$O—C$_6$H$_4$ | H | 67 | 85 | 382.9 |
| 10a | C$_6$H$_5$CH$_2$ | CH$_3$CH$_2$ | CH$_3$ | 58 | 76 | 318.7 |
| 10b | C$_6$H$_5$CH$_2$ | C$_6$H$_5$ | CH$_3$ | 62 | 79 | 366.8 |
| 10c | CH$_3$ | C$_6$H$_5$ | CH$_3$ | 63 | 82 | 290.7 |
| 10d | H | C$_6$H$_5$ | CH$_3$ | 65 | 73 | 276.8 |

TABLE 1-continued

Individual 1,3-disubstituted and 1,3,5-trisubstituted-1,3,5-triazine-2,4,6-trione Compounds 8,10 from p-methylbenzhydrylamine MBHA Resin

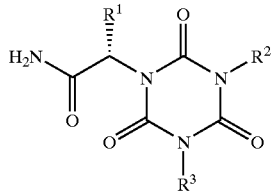

| Product | $R^1$ | $R^2$ | $R^3$ | Yield[a] | Purity[b] | MW(found)[c] ([M + H]$^+$) |
|---|---|---|---|---|---|---|
| 10e | $CH_3$ | $C_6H_5$ | $CH_3CH_2$ | 62 | 88 | 304.7 |
| 10f | $CH_3$ | $C_6H_5$ | $C_6H_5CH_2$ | 58 | 93 | 366.8 |
| 10g | $CH_3$ | $C_6H_5$ | p-Br—$C_6H_4CH_2$ | 61 | 91 | 445.2 |
| 10h | $CH_3$ | $C_6H_5$ | 2-$CH_3$—$C_6H_4CH_2$ | 56 | 96 | 381.1 |
| 10i | $C_6H_5CH_2$ | $C_6H_5$ | p-Br—$C_6H_4CH_2$ | 67 | 82 | 521.8 |
| 10j | $C_6H_5CH_2$ | p-Cl-$C_6H_4$ | $CH_3$ | 71 | 76 | 400.8 |

[a]Yields (in %) are based on the weight of crude material and are relative to the initial loading of the resin. The isolated yields are listed in the experimental section.
[b]The purity of the crude material was estimated based on analytical traces at $\lambda$ = 214 nm.
[c]Confirmed by mass spectra (ESI).

Interestingly, the benzyl-substituted products were stable under the HF cleavage conditions used. O-Alkylation and amide-alkylation derivatives were not detected from LC-MS and NMR. In addition, no racemization was observed from $^1$H-NMR, and chiral HPLC. It is noteworthy that the nature of the substituents ($R^2$) of the ureas appeared to have little effect on the cyclization reaction. Both aryl and alkyl ($R^2$) substituents of the ureas could be used in conjunction with the cyclization to create a variety of 1,3,5-disubstituted-1,3,5-triazine-2,4,6-triones.

To prepare a set of sub-libraries using the above synthetic scheme, each of the reversibly-linked solid phase bound-compounds with the first defined variable group (e.g. amino acid side chain $R^1$) is reacted separately with an isocyanate having a second variable group (substituent $R^2$) group to form a plurality of separate solid phase-bound disubstituted ureas such as Compound 6 that have the same $R^1$ and different $R^2$ groups. Equimolar amounts of each of those disubstituted ureas are homogeneously admixed together and then reacted with chlorocarbonylisocyanate to form a mixture of solid phase-bound 1,3-disubstituted-triazinetriones such as Compound 7 in which each $R^1$ group is the same and the $R^2$ groups are a mixture of equimolar amounts of each of the different $R^2$ groups used. The disubstituted ureas can also be separately reacted with chlorocarbonylisocyanate, followed by admixture to homogeneity to provide the same resultant mixture of solid phase-bound 1,3-disubstituted-triazinetriones.

An aliquot of solid phase-bound 1,3-disubstituted-2,4,6-triazinetriones is then reacted with each of the desired alkylating agents to form a plurality of separate solid phase-bound 1,3,5-trisubstituted-2,4,6-triazinetriones such as Compound 9. Homogeneous admixture of equimolar amounts of the separate solid phase-bound 1,3,5-trisubstituted-2,4,6-triazinetriones provides a sub-library of solid phase-bound 1,3,5-trisubstituted-2,4,6-triazinetriones whose first substituent ($R^1$) is the same for each and wherein each of the other two substituent positions is occupied by an equimolar mixture of substituent groups ($R^2$ and $R^3$). Addition of an equimolar amount of the solid phase-bound 1,3-disubstituted-2,4,6-triazinetrione used for the alkylation reaction adds a mixture having hydrido as the and $R^3$ group. A sub-library free of the solid phase support can be provided by cleavage from the solid phase support before or after admixture of the solid phase-bound precursors.

Further sub-libraries can be similarly prepared starting with a different solid phase-bound amino acid. Those sub-libraries are each assayed to define the identity of the first variable substituent ($R^1$) that exhibits the highest activity in the screening assay of choice.

Upon determining the identity of the first variable substituent that provides the highest activity, a new set of sub-libraries is prepared in which the first variable substituent is held constant, the second variable substituent ($R^2$) is varied individually in each sub-library set, and the third variable substituent is occupied by an equimolar mixture of the substituent groups. These sub-libraries each having the same $R^1$ group, separate and different $R^2$ substituents and mixed $R^3$ substituents are each assayed to define the identity of the second variable substituent ($R^2$) that exhibits the highest activity in the screening assay of choice.

A new sub-library with the first two variable positions defined is separately reacted with each of the other possibilities at the remaining undefined variable position, $R^3$. As before, the identity of the third variable position in the sub-library having the highest activity is determined.

It is to be understood that the order of defining the substituents at each position discussed above is provided for illustrative purposes and can be varied as desired. In addition, the preparation of a library or sub-libraries using the synthesis procedures described below can also be used.

C. 1,3-Disubstituted-1,3,5-triazine-2,4,6-trione and 1,3,5-tisubstituted-1,3,5-triazine-2,4,6-trione from Hydroxymethyl Polystyrene (Wang) Resin Synthesize of 1,3,5-trisubstituted-1,3,5-triazine-2,4,6-triones bearing a carboxylic acid through the use of Wang resin has also been examined. Using the analogous protocol, an Fmoc-protected amino acid was attached to the Wang resin using N, N-diisopropyldiimide (DIC) and 4-dimethylaminopyridine (DMAP) as coupling reagents in DCM/DMF (5:1). The process was repeated twice to give the resin-bound Fmoc-protected amino acid 11 Compound [Albericio et al., *J. Comb. Chem.* 2001, 3, 290], as is outlined in Scheme 3, below.

Scheme 3

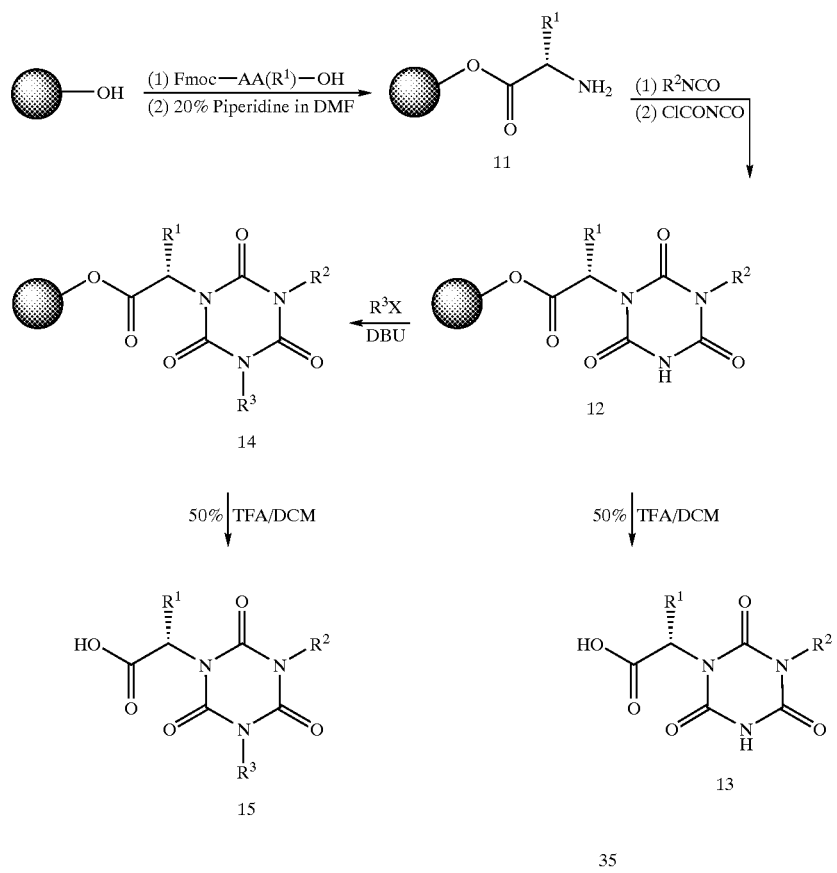

In accordance with Scheme 3, the Fmoc group was removed using 20 percent piperidine in DMF. The free amine (Compound 11) was reacted with isocyanate to form resin-bound urea. Treatment of the resin-bound urea with chlorocarbonylisocyanate yielded the 1,3-disubstituted-1,3,5-triazine-2,4,6-trione Compound 12. Product Compound 13 was obtained following cleavage from the resin by treatment with trifluoroacetic acid (TFA) in methylene chloride (DCM).

The resin-bound 1,3-disubstituted-1,3-triazine-2,4,6-trione Compound 12 was alkylated with alkyl halides in the presence of DBU to yield 1,3,5-triazine-2,4,6-trione Compounds 14. Upon treatment with trifluoroacetic acid in methylene chloride, the desired product Compound 15 was obtained in good yield and purity (Table 2). From the results obtained, the ester linker of Wang resin was stable under the cyclization and alkylation reaction conditions used.

TABLE 2

Individual 1,3-disubstituted and 1,3,5-trisubstituted-1,3,5-triazine-2,4,6-trione Compounds 13,15 from hydroxymethyl polystyrene Wang Resin

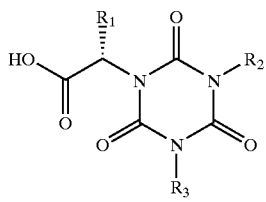

| Product | $R^1$ | $R^2$ | $R^3$ | Yield[a] | Purity[b] | MW(found)[c] ([M + H]+) |
|---------|-------|-------|-------|----------|-----------|-------------------------|
| 13a | $(CH_3)_2CH$ | p-Cl-$C_6H_4$ | H | 75 | 81 | 334.0 |
| 13b | $(CH_3)_2CH$ | p-$CH_3$—$C_6H_4$ | H | 76 | 86 | 320.1 |
| 13c | $C_6H_5CH_2$ | p-$CH_3O$—$C_6H_4$ | H | 78 | 88 | 384.1 |
| 15a | $(CH_3)_2CH$ | $C_6H_5$ | $C_6H_5CH_2$ | 82 | 87 | 395.9 |
| 15b | $(CH_3)_2CH$ | $C_6H_5$ | 2-$CH_3$—$C_6H_4CH_2$ | 75 | 82 | 410.0 |

TABLE 2-continued

Individual 1,3-disubstituted and 1,3,5-trisubstituted-
1,3,5-triazine-2,4,6-trione Compounds 13,15 from
hydroxymethyl polystyrene Wang Resin

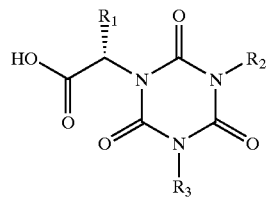

| Product | $R^1$ | $R^2$ | $R^3$ | Yield[a] | Purity[b] | MW(found)[c] ([M + H]⁺) |
|---|---|---|---|---|---|---|
| 15c | $C_6H_5CH_2$ | $CH_3CH_2$ | $CH_3CH_2$ | 75 | 85 | 334.0 |
| 15d | $C_6H_5CH_2$ | $CH_3CH_2$ | $CH_2CHCH_2$ | 78 | 86 | 346.0 |
| 15e | $C_6H_5CH_2$ | $CH_3CH_2$ | 2-$CH_3$—$C_6H_4CH_2$ | 72 | 91 | 409.9 |
| 15f | $C_6H_5CH_2$ | $CH_3CH_2$ | p-$NO_2$—$C_6H_4CH_2$ | 79 | 92 | 440.7 |

[a]Yields (in percent) are based on the weight of crude material and are relative to the initial loading of the resin. The isolated yields are listed in the experimental section.
[b]The purity of the crude material was estimated based on analytical traces at λ = 214 nm.
[c]Confirmed by mass spectra (ESI)

Using the concept of "libraries from libraries", [Ostresh et al., Proc. Natl. Acad. Sci. U.S.A. 1994, 91, 11138] 1,3-disubstituted and 1,3,5-trisubstituted-1,3,5-triazine-2,4,6-triones have been prepared on two different solid supports from common building blocks such as amino acids ($R^1$), isocyanates ($R^2$) and alkyl halides ($R^3$). This synthetic method is well suited for combinatorial library synthesis of a diverse collection of structurally novel triazinetriones with potential for anti-coccidial activity.

Experimental Section p-Methylbenzhydrylamine (MBHA) resin, 1% divinylbenzene, 100–200 mesh, 1 meq/g substitution, Hydroxymethyl polystyrene (Wang) resin, 1% divinylbenzene, 100–200 mesh, 0.96 meq/g substitution, and N,N'-diisopropylcarbodiimide (DIC) were purchased from Chem Impex Intl. (Wood Dale, Ill.). Boc-amino acid derivatives, and N-hydroxy-benzotriazole (HOBt) were purchased from Calbiochem-Novabiochem Corp. (San Diego, Calif.) and Bachem Bioscience Inc. (Philadelphia, Pa.). Trifluoroacetic acid (TFA) and HF were purchased from Halocarbon (River Edge, N.J.) and Air Products (San Marcos, Calif.), respectively. All other reagents and anhydrous solvents were purchased from Aldrich Chemical Co. (Milwaukee, Wis.). Analytical RP-HPLC was performed on a Beckman System Gold Instrument (Fullerton, Calif.). Samples were analyzed using a Vydac 218TP54 C18 column (0.46×25 cm). LC-MS (APCI) was recorded on a Finnigan Mat LCQ mass spectrometer (ThermoQuest Corporation, CA.) at 214 nm using a Betasil C18, 3 μm, 100 Å, 3×50 mm column. Preparative RP-HPLC was performed on a Waters DeltaPrep preparative HPLC (Millipore) using a Vydac 218TP1022 C18 column (2.2×25 cm).

EXAMPLE 1

Typical Procedure for the Individual Synthesis of 1,3-disubstituted-1,3,5-triazine-2,4,6-trione (8) from p-methylbenzhydrylamine (MBHA) Resin A polypropylene mesh packet was sealed with 100 mg of MBHA resin (1 meq/g, 100–200 mesh). [Houghten, Proc. Natl. Acad. Sci. U.S.A. 1985, 82, 5131.] Reactions were carried out in polypropylene bottles. The resin was washed with dichloromethane (DCM) followed by neutralization with 5% diisopropylethylamine (DIEA) in DCM and washed with DCM.

The first Boc-L-amino acid (6 equivalents, 0.1M) was coupled using DIC (6 equivalents, 0.1M) and HOBt (6 equivalents, 0.1M) in anhydrous DMF for 2 hours. The resin was washed with DMF (3 times), DCM (3 times), MeOH (3 times) and the Boc deprotection was performed using 55% TFA in DCM for 30 minutes, followed by washing with DCM (2 times), 2-propanol (IPA) (2 times), and DCM (2 times). After neutralization, the resin was treated with isocyanate (6 equivalents) in anhydrous DCM overnight (about 18 hours) to yield the ureas. Completeness of the coupling was verified by the ninhydrin test. The resin was washed with DCM (2 times), IPA (2 times), and DCM (2 times).

The resin-bound urea was reacted with chlorocarbonyl-isocyanate (6 equivalents, 0.1M) in anhydrous in toluene at 65° C. for 7 hours to yield the resin-bound 1,3-disubstituted-1,3,5-triazine-2,4,6-trione Compounds 7. After washing with DMF (3 times), DCM (3 times), MeOH (3 times), the resin was cleaved by anhydrous HF at 0° C. for 1.5 hours [Houghten et al., J. Int. J. Pept. Protein Res. 1986, 27, 6763] and the cyclization product was extracted with 95% acetic acid in $H_2O$ and lyophilized. Following purification by RP-HPLC, the product was characterized by electrospray LC-MS and $^1H$ and $^{13}C$ NMR.

Selective N-alkylation of 1,3-disubstituted-1,3,5-triazine-2,4,6-trione (Compound 10)

To the resin Compound 7 in THF was added 1,8-diazabicyclo[5.4.0]undec-7-ene (DBU, 10 equivalents, 0.1M). After shaking 30 minutes and excess base was removed by cannulation, the individual alkylating agent (5 equivalents, 0.1M) in DMSO was added. The solution was vigorously shaken for 4 hours at room temperature. After washing with DMF (3 times), DCM(3 times), MeOH (3 times), the resin was cleaved by anhydrous HF at zero degrees C. for 1.5 hours, and the product Compound 10 was extracted with 95 percent acetic acid in $H_2O$ and lyophilized. Following purification by RP-HPLC, the product was characterized by electrospray LC-MS and $^1H$ and $^{13}C$ NMR.

Procedure for Synthesis of a 1,3,5-trisubstituted-1,3,5-triazine-2,4,6-trione from Hydroxymethyl Polystyrene (Wang) Resin (Compounds 13 and 15)

A polypropylene mesh packet was sealed with 100 mg of Wang resin (0.94 meq/g, 100–200 mesh). Reactions were carried out in polypropylene bottles. A solution of N-Fmoc-L-amino acid (3 equivalents, 0.1M), DMAP (0.3 equivalents), and DIC (3 equivalents, 0.1M) in anhydrous DCM/DMF (5:1) was added to the resin. The mixture was shaken at room temperature for 2 hours. The resin was washed with DMF (3 times), $CH_2Cl_2$ (3 times). The overall process was repeated to afford Compound 11. The Fmoc deprotection was performed using 20 percent piperidine in DMF for 30 minutes, followed by washing with DCM (2 times), 2-propanol (IPA) (2 times), and DCM (2 times).

The resin was treated with isocyanate (6 equivalents, 0.1M) in anhydrous DCM overnight (about 18 hours) to yield the resin-bound urea. The resin-bound urea was reacted with chlorocarbonylisocyanate (6 equivalents, 0.1M) in anhydrous toluene at 65° C. for 7 hours to yield the resin-bound 1,3-disubstituted-1,3,5-triazine-2,4,6-triones Compound 12. After washing with DMF (3 times), MeOH (3 times), DCM (3 times), the resin was cleaved with 50 percent TFA/DCM for 1 hour. The resulting solution was concentrated to give the cyclization product Compound 13.

The resin-bound 1,3-disubstituted-1,3,5-triazine-2,4,6-trione Compound 12 was added 1,8-diazabicyclo[5.4.0]undec-7-ene (DBU, 10 equivalents, 0.1M) in THF. The reaction was shaken for 30 minutes and drained. The individual alkylating agent (5 equivalents, 0.1M) in DMSO was added. The solution was vigorously shaken for 4 hours at room temperature. After washing with DMF (3 times), DCM (3 times), MeOH (3 times), the resin was cleaved with 50% TFA/DCM for 1 hour. The solution was concentrated to give the product Compound 15. Following purification by RP-HPLC, the product was characterized by electrospray LC-MS and $^1H$ and $^{13}C$ NMR.

Analytical Data for Selected Compounds (2S)-3-phenyl-2-(2,4,6-trioxo-3-phenyl-1,3,5-triazinan-1-yl)propanamide (8a): yield 32%. LC-MS (ESI) m/z 352.9 (M+H$^+$). $^1H$ NMR (500 MHz, CDCl$_3$): δ 3.35–3.40 (m, 2H), 5.5–5.53 (t, J=7.5 Hz, 1H), 6.43 (s, 1H), 6.69 (s, 1H), 6.97 (s, 2H), 7.14–7.15 (d, J=6.8 Hz, 2H), 7.26–7.39(m, 6H), 9.63 (s, 1H). $^{13}C$ NMR (125 MHz, CDCl$_3$): δ 34.4, 56.9, 127.5, 128.4, 129.2, 129.3, 129.7, 129.8, 133.1, 135.9, 148.3, 148.6, 149.6, 172.6.

(2S)-2-[3-(4-chlorophenyl)-2,4,6-trioxo-1,3,5-triazinan-1-yl]-3-phenylpropanamide (8b): yield 28%. LC-MS (ESI) m/z 387.5 (M+H$^+$). $^1H$ NMR (500 MHz, CDCl$_3$): δ3.32–3.38 (m, 2H), 5.51–5.54 (t, J=7.5 Hz, 1H), 6.54 (s, 1H), 6.71 (s, 1H), 6.84 (s, 2H), 7.12 (s, 2H), 7.26–7.29(m, 5H), 10.02 (s, 1H). $^{13}C$ NMR (125 MHz, CDCl$_3$): δ34.4, 56.9, 127.7, 129.2, 129.8, 131.5, 135.7, 135.8, 148.2, 148.7, 149.5, 172.5.

(2S)-2-[3-(4-methoxyphenyl)-2,4,6-trioxo-1,3,5-triazinan-1-yl]-3-phenylpropanamide (8c): yield 41%. LC-MS (ESI) m/z 382.9 (M+H$^+$). $^1H$ NMR (500 MHz, CDCl$_3$): δ 3.33–3.39 (m, 2H), 3.75 (s, 1H), 5.51–5.55 (t, J=7.5 Hz, 1H), 6.51 (s, 1H), 6.67 (s, 1H), 6.86 (s, 4H), 7.12–7.27(m, 5H), 9.77 (s, 1H). $^{13}C$ NMR (125 MHz, CDCl$_3$): δ34.3, 55.6, 56.9, 114.9, 125.5, 127.6, 129.1, 129.3, 129.5, 136.1, 148.6, 148.7, 149.8, 160.3, 172.5.

(2S)-2-(3-ethyl-5-methyl-2,4,6-trioxo-1,3,5-triazinan-1-yl)-3-phenylpropanamide (10a): yield 38%. LC-MS (ESI) m/z 318.7 (M+H$^+$). $^1H$ NMR (500 MHz, CDCl$_3$): δ 1.09–1.12 (t, J=7.1 Hz, 3H), 3.25 (s, 3H), 3.44–3.47 (m, 2H), 3.82–3.86 (q, J=7.1 Hz, 2H), 5.51–5.65 (t, J=7.5 Hz, 1H), 5.99 (s, 1H), 6.31 (s, 1H), 7.16–7.29(m, 5H). $^{13}C$ NMR (125 MHz, CDCl$_3$): δ13.0, 29.5, 34.8, 38.7, 57.3,127.7, 129.1, 129.2, 136.0, 148.7, 149.1, 171.8.

(2S)-2-(3-methyl-2,4,6-trioxo-5-phenyl-1,3,5-triazinan-1-yl)-3-phenylpropanamide (10b): yield 41%. LC-MS (ESI) m/z 366.8 (M+H$^+$). $^1H$ NMR (500 MHz, CDCl$_3$): δ 3.31 (s, 3H), 3.48–3.49 (d, J=8.3 Hz, 2H), 5.67–5.71 (t, J=7.5 Hz, 1H), 6.03 (s, 1H), 6.45 (s, 1H), 7.07–7.48(m, 10H). $^{13}C$ NMR (125 MHz, CDCl$_3$): δ 29.9, 34.8, 57.5, 127.9, 128.4, 129.2, 129.3, 129.7, 133.7, 135.9, 148.8, 148.9, 149.1, 171.9.

(2S)-2-(3-methyl-2,4,6-trioxo-5-phenyl-1,3,5-triazinan-1-yl)propanamide (10c): yield 36%. LC-MS (ESI) m/z 290.7 (M+H$^+$). $^1H$ NMR (500 MHz, CDCl$_3$): δ 1.69–1.71 (d, J=6.9 Hz, 3H), 3.39 (s, 3H), 5.39–5.43 (q, J=7.1 Hz, 1H), 5.99 (s, 1H), 6.18 (s, 1H), 7.26–7.51 (m, 5H). $^{13}C$ NMR (125 MHz, CDCl$_3$): δ 15.1, 29.9, 52.6, 128.6, 129.7, 129.8, 133.5, 148.8, 149.1, 172.4.

2-(3-methyl-2,4,6-trioxo-5-phenyl-1,3,5-triazinan-1-yl)acetamide (10d): yield 33%. LC-MS (ESI) m/z 276.8 (M+H$^+$). $^1H$ NMR (500 MHz, CDCl$_3$): 3.39 (s, 3H), 4.58 (s, 2H), 5.84 (brs, 1H), 7.26–7.49 (m, 5H). $^{13}C$ NMR (125 MHz, CDCl$_3$): δ 29.9, 44.6, 128.6, 129.6, 129.7, 133.9, 149.2, 149.4, 168.5.

(2S)-2-(3-ethyl-2,4,6-trioxo-5-phenyl-1,3,5-triazinan-1-yl)propanamide (10e): yield 47%. LC-MS (ESI) m/z 304.7 (M+H$^+$). $^1H$ NMR (500 MHz, CDCl$_3$): δ 1.28–1.31 (t, J=7.1 Hz, 3H), 1.69–1.71 (d, J=7.0 Hz, 3H), 3.98–4.02 (q, J=7.0 Hz, 2H), 5.39–5.43 (q, J=7.1 Hz, 1H), 5.95 (s, 1H), 6.15 (s, 1H), 7.25–7.50 (m, 5H). $^{13}C$ NMR (125 MHz, CDCl$_3$): δ 13.3, 15.1, 39.2, 52.5, 128.6, 129.6, 129.7, 133.8, 148.6, 148.7, 148.9, 172.3.

(2S)-2-(3-benzyl-2,4,6-trioxo-5-phenyl-1,3,5-triazinan-1-yl)propanamide (10f): yield 48%. LC-MS (ESI) m/z 366.8 (M+H$^+$). $^1H$ NMR (500 MHz, CDCl$_3$): δ1.69–1.70 (d, J=7.0 Hz, 3H), 5.06–5.12 (m, 2H), 5.39–5.43 (q, J=7.0 Hz, 1H), 5.97 (s, 1H), 6.44 (s, 1H), 7.25–7.50 (m, 10H). $^{13}C$ NMR (125 MHz, CDCl$_3$): δ15.0, 46.8, 52.6, 128.6, 128.9, 129.7, 133.7, 135.6, 148.7, 148.9, 149.0, 172.7.

(2S)-2-[3-(4-bromobenzyl)-2,4,6-trioxo-5-phenyl-1,3,5-triazinan-1-yl]propanamide (10g): yield 43%. LC-MS (ESI) m/z 445.2 (M+H$^+$). $^1H$ NMR (500 MHz, CDCl$_3$): δ 1.69–1.71 (d, J=7.0 Hz, 3H), 5.06–5.12 (dd, J=5.2, 14.1 Hz, 2H), 5.39–5.44 (q, J=7.0 Hz, 1H), 5.98 (s, 1H), 6.60 (s, 1H), 7.25–7.50 (m, 9H). $^{13}C$ NMR (125 MHz, CDCl$_3$): δ 15.1, 46.2, 52.7, 122.8, 128.5, 129.7, 131.5, 132.1, 133.6, 134.5, 148.6, 148.8, 148.9, 172.7.

(2S)-2-[3-(2-methylbenzyl)-2,4,6-trioxo-5-phenyl-1,3,5-triazinan-1-yl]propanamide (10h): yield 38%. LC-MS (ESI) m/z 381.1 (M+H$^+$). $^1H$ NMR (500 MHz, CDCl$_3$): δ 1.69–1.71 (d, J=7.0 Hz, 3H), 2.42 (s, 3H), 5.12 (s, 2H), 5.42–5.46 (q, J=7.0 Hz, 1H), 6.08 (s, 1H), 6.83 (s, 1H), 7.16–7.50 (m, 9H). $^{13}C$ NMR (125 MHz, CDCl$_3$): δ 14.9, 19.5, 44.1, 52.6, 126.5, 127.1, 128.1, 128.5, 129.7, 130.8, 133.6, 133.7, 136.4, 148.8, 148.9, 149.1, 173.6.

(2S)-2-[3-(4-bromobenzyl)-2,4,6-trioxo-5-phenyl-1,3,5-triazinan-1-yl]propanamide (10i): yield 36%. LC-MS (ESI) m/z 521.8 (M+H$^+$). $^1H$ NMR (500 MHz, CDCl$_3$): δ 3.39–3.48(m, 2H), 4.86–4.98 (dd, J=14.2, 33.5 Hz, 2H), 5.65–5.68 (dd, J=2.6, 7.1 Hz, 1H), 6.14 (s, 1H), 6.74 (s, 1H), 7.05–7.46 (m, 14H). $^{13}C$ NMR (125 MHz, CDCl$_3$): δ 34.4, 45.9, 57.3, 122.6, 127.7, 128.3, 129.1, 129.7, 131.1, 131.9, 133.5, 134.4, 135.4, 148.6, 148.7, 148.8, 172.5.

(2S)-2-[3-(4-chlorophenyl)-5-methyl-2,4,6-trioxo-1,3,5-triazinan-1-yl]-3-phenylpropanamide (10j): yield 31%. LC-MS (ESI) m/z 400.8(M+H$^+$). $^1$H NMR (500 MHz, CDCl$_3$): δ3.31(s, 3H), 3.47–3.49 (d, J=8.3 Hz, 2H), 5.66–5.69 (t, J=8.4 Hz, 1H), 6.06 (s, 1H), 6.63 (s, 1H), 7.00–7.43 (m, 9H). $^{13}$C NMR (125 MHz, CDCl$_3$): δ 29.9, 34.8, 57.4, 127.9, 129.2, 129.3, 129.8, 129.9, 132.1, 135.7, 135.8, 148.6, 148.7, 148.9, 172.2.

(2S)-2-[3-(4-chlorophenyl)-2,4,6-trioxo-1,3,5-triazinan-1-yl]-3-methylbutanoic acid (13a): yield 28%. LC-MS (ESI) m/z 340.1(M+H$^+$). $^1$H NMR (500 MHz, CDCl$_3$): δ 0.89 (d, J=6.9 Hz, 3H), 1.21 (d, J=6.9 Hz, 3H), 2.66 (m, 1H), 4.93 (d, J=9.1 Hz, 1H), 7.16–7.18(d, J=8.4 Hz, 2H), 7.42–7.44(d, J=8.4 Hz, 2H), 9.47 (brs, 1H). $^{13}$C NMR (125 MHz, CDCl$_3$): δ 19.3, 21.9, 27.9, 60.8,129.9, 130.0, 131.4, 135.9, 148.1, 148.5, 149.5, 173.0.

(2S)-3-methyl-2-[3-(4-methylphenyl)-2,4,6-trioxo-1,3,5-triazinan-1-yl]butanoic acid (13b): yield 32%. LC-MS (ESI) m/z 320.1(M+H$^+$). $^1$H NMR (500 MHz, CDCl$_3$): δ 0.90 (d, J=6.8 Hz, 3H), 1.21 (d, J=6.8 Hz, 3H), 2.39 (s, 1H), 2.66 (m, 1H), 4.934(d, J=9.2 Hz, 1H), 7.11–7.12 (d, J=8.2 Hz, 2H), 7.26–7.28 (d, J=8.2 Hz, 2H), 9.44 (brs, 1H). $^{13}$C NMR (125 MHz, CDCl$_3$): δ 19.3, 21.5, 22.0, 27.6, 60.7, 128.2, 130.4, 130.5, 140.0, 148.5, 148.7, 149.8, 173.2.

(2S)-2-[3-(4-methoxyphenyl)-2,4,6-trioxo-1,3,5-triazinan-1-yl]-3-phenylpropanoic acid (13c): yield 35%.LC-MS (ESI) m/z 384.1(M+H$^+$). $^1$H NMR (500 MHz, CDCl$_3$): δ 3.40–3.45 (m, 1H), 3.50–3.54 (m, 1H), 3.78 (s, 1H), 5.61–5.64(dd, J=5.1, 5.7 Hz, 1H), 6.89 (s, 4H), 7.16–7.31 (m, 4H), 9.32 (brs, 1H). $^{13}$C NMR (125 MHz, CDCl$_3$): δ 34.4, 55.7, 56.2, 114.9, 125.4, 127.5, 128.9, 129.4, 129.5, 136.2, 148.3, 148.4, 149.5, 160.3, 172.8.

(2S)-2-(3-benzyl-2,4,6-trioxo-5-phenyl-1,3,5-triazinan-1-yl)-3-methylbutanoic acid (15a): yield 35%.LC-MS (ESI) m/z 395.9(M+H$^+$). $^1$H NMR (500 MHz, CDCl$_3$): δ 0.88 (d, J=6.8 Hz, 3H), 1.23 (d, J=6.8 Hz, 3H), 2.71 (m, 1H), 5.03(d, J=9.2 Hz, 1H), 5.11(d, J=7.6 Hz, 2H), 7.23–7.26 (m, 2H), 7.31–7.35 (m, 2H), 7.43–7.49 (m, 4H), 9.44 (brs, 1H). $^{13}$C NMR (125 MHz, CDCl$_3$): δ19.2, 22.1, 27.9, 46.8, 51.1, 128.5, 128.9, 129.3, 129.7, 133.7, 135.7, 148.8, 148.9, 149.3, 173.6.

(2S)-3-methyl-2-[3-(2-methylbenzyl)-2,4,6-trioxo-5-phenyl-1,3,5-triazinan-1-yl]butanoic acid (15b): yield 38%.LC-MS (ESI) m/z 410.1(M+H$^+$). $^1$H NMR (500 MHz, CDCl$_3$): δ 0.91 (d, J=7.0 Hz, 3H), 1.25 (d, J=7.0 Hz, 3H), 2.42 (s, 3H), 2.73 (m, 1H), 5.04(d, J=9.2 Hz, 1H), 5.15 (s, 2H), 7.17–7.25 (m, 9H). $^{13}$C NMR (125 MHz, CDCl$_3$): δ 19.3, 19.5, 22.1, 27.9, 29.9, 44.2, 61.2, 126.5, 126.7, 127.9, 128.5, 129.7, 130.8, 133.6, 133.7, 136.3, 148.9, 149.0, 149.4, 173.1.

(2S)-2-(3,5-diethyl-2,4,6-trioxo-1,3,5-triazinan-1-yl)-3-phenylpropanoic acid (15c): yield 38%.LC-MS (ESI) m/z 334.0(M+H$^+$). $^1$H NMR (500 MHz, CDCl$_3$): δ 1.10 (t, J=6.9 Hz, 6H), 3.41–3.54 (m, 2H), 3.81–3.86 (dd, J=7.0, 7.2 Hz, 4H), 5.65–5.68 (dd, J=4.8, 5.8 Hz, 1H), 7.12–7.25 (m, 5H). $^{13}$C NMR (125 MHz, CDCl$_3$): δ 13.1, 34.4, 38.5, 56.0, 127.3, 128.8, 129.3, 136.3, 148.3, 148.4, 173.9.

(2S)-2-(3-allyl-5-ethyl-2,4,6-trioxo-1,3,5-triazinan-1-yl)-3-phenylpropanoic acid (15d): yield 41%.LC-MS (ESI) m/z 346.0(M+H$^+$). $^1$H NMR (500 MHz, CDCl$_3$): δ1.09 (t, J=6.9 Hz, 3H), 3.41–3.55 (m, 2H), 3.81–3.86 (dd, J=7.0, 7.2 Hz, 2H), 4.38(d, J=7.0 Hz, 2H), 5.16(d, J=10.2 Hz, 1H), 5.65–5.68 (dd, J=4.8, 5.8 Hz, 1H), 5.71–5.75 (m, 2H), 7.12–7.25 (m, 5H). $^{13}$C NMR (125 MHz, CDCl$_3$): δ13.1, 34.4, 38.6, 44.9, 56.1, 118.5, 127.3, 128.8, 129.3, 130.7, 136.2, 148.2, 148.4, 148.5, 173.9.

(2S)-2-[3-ethyl-5-(2-methylbenzyl)-2,4,6-trioxo-1,3,5-triazinan-1-yl]-3-phenylpropanoic acid (15e): yield 39%.LC-MS (ESI) m/z 409.9 (M+H$^+$). $^1$H NMR (500 MHz, CDCl$_3$): δ 1.11 (t, J=6.9 Hz, 3H), 2.35 (s, 2H), 3.47–3.51 (m 2H), 3.84–3.88 (dd, J=7.0, 7.2 Hz, 2H), 4.92–5.01 (dd, J=11.3, 15.4 Hz, 2H), 5.72–5.75 (dd, J=4.8, 5.8 Hz, 1H), 7.09–7.26 (m, 9H). $^{13}$C NMR (125 MHz, CDCl$_3$): δ 13.1, 19.4, 29.9, 34.3, 38.7, 43.8, 56.1, 125.9, 126.4, 127.3, 127.7, 128.8, 129.3, 130.7, 133.5, 135.9, 136.1, 148.3, 148.5, 148.9, 173.8.

(2S)-2-[3-ethyl-5-(4-nitrobenzyl)-2,4,6-trioxo-1,3,5-triazinan-1-yl]-3-phenylpropanoic acid (15f): yield 42%.LC-MS (ESI) m/z 440.7 (M+H$^+$). $^1$H NMR (500 MHz, CDCl$_3$): δ 1.11 (t, J=6.8 Hz, 3H), 3.41–3.55 (m, 2H) 3.41–3.46 (m, 1H), 3.51–3.56 (dd, J=5.6, 8.5 Hz, 1H), 3.83–3.88 (dd, J=7.0, 7.2 Hz, 2H), 4.98(d, J=14.8 Hz, 2H), 5.06(d, J=14.8 Hz, 1H), 5.68–5.71 (dd, J=4.8, 5.8 Hz, 1H), 7.05–7.32 (m, 7H), 8.15 (d, J=8.4 Hz, 2H). $^{13}$C NMR (125 MHz, CDCl$_3$): δ 13.0, 34.3, 38.9, 45.5, 56.3, 124.1, 127.4, 128.8, 129.2, 129.3, 135.9, 142.7, 147.9, 148.1, 148.4, 148.7, 173.8.

EXAMPLE 2

Library Preparation

Libraries of triazinetrione compounds were prepared analogously to the preparation of individual compounds discussed before following the procedures of Scheme 3. The library was prepared in an iterative format in which the R$^1$ position was a mixture of functionalities, whereas the other two positions were defined.

Twenty-six amino acids were used to incorporate the R$^1$ functionality, 20 isocyanates to incorporate the R$^2$ functionality, and 20 alkyl halides were used to incorporate the R$^3$ functionality. Thus, equimolar amounts of each of the 26 products of the first reaction (Compound 11 of Scheme 3) were mixed homogeneously together.

That mixture was divided into 400 aliquots for the next reaction step of individual reactions with each of the twenty isocyanates to form twenty sets of twenty identical mixture products that were thereafter cyclized to form products corresponding to Compound 12 in which the R$^1$ substituent was an equimolar mixture of substituents and each R$^2$ substituent was a single group. Each of the mixture products corresponding to Compound 12 was reacted with one of nineteen alkylating agents to provide 380 (19×20) mixtures of compounds corresponding to Compound 14. The set of twenty compound mixtures that were unreacted in the last step contained hydrido R$^3$ group of Compound 12. The products were cleaved from the solid phase resin to form 380 mixtures corresponding to Compounds 15 and 20 mixtures corresponding to 13, respectively.

The library was thereby composed of 400 mixtures corresponding to the 400 (20×20) possible combinations of defined substituents at the R$^2$ and R$^3$ positions, with mixtures of original 26 R$^1$ substituents derived from the 26 amino acids reacted to form the R$^1$ position.

As noted before, the mixture at the R$^1$ position was accomplished by coupling each of the protected amino acids to equal aliquots of Wang resin and then mixing the resin (known as the split resin method of incorporating mixtures). The R groups utilized for this study are listed in the Table below.

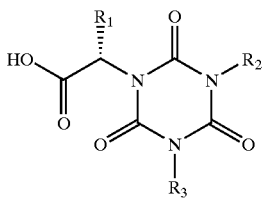

| | R[1] (Amino Acid Side Chain) | R[2] Isocyanate | R[3]* |
|---|---|---|---|
| 1 | L-Alanine | Phenyl | H |
| 2 | D-Alanine | 2-Methoxyphenyl | Methyl |
| 3 | L-Phenylalanine | 3-Methoxyphenyl | Benzyl |
| 4 | D-Phenylalanine | 4-Methoxyphenyl | 2-Methylbenzyl |
| 5 | Glycine | o-Tolyl | 3-Methylbenzyl |
| 6 | Isoleucine | m-Tolyl | 4-Methylbenzyl |
| 7 | L-Leucine | p-Tolyl | 2-Fluorobenzyl |
| 8 | D-Leucine | 4-Flouorophenyl | 3-Fluorobenzyl |
| 9 | L-4-Chloro-phenylalanine | 4-Chlorophenyl | 4-Fluorobenzyl |
| 10 | D-4-Chloro-phenylalanine | 4-Bromophenyl | 2-Chlorobenzyl |
| 11 | L-4-Fluoro-phenylalanine | 3-Chloro-4-methylphenyl | 3-Chlorobenzyl |
| 12 | D-4-Fluoro-phenylalanine | 3,4-(Methylene-dioxy)phenyl | 2,4-Difluorobenzyl |
| 13 | L-4-Nitro-phenylalanine | 4-Phenoxyphenyl | 3,4-Difluorobenzyl |
| 14 | L-4-Nitro-phenylalanine | 4-Ethylphenyl | 3,5-Difluorobenzyl |
| 15 | L-Cyclohexyl-glycine | α,α,α-Trifluoro-p-tolyl | 2,6-Difluorobenzyl |
| 16 | D-Cyclohexyl-glycine | 2,5-Dimethylphenyl | 4-(Trifluoromethoxy)-benzyl |
| 17 | L-Cyclohexyl-alanine | Ethyl | 3-Methoxybenzyl |
| 18 | D-Cyclohexyl-alanine | Butyl | 3,5-Dimethoxybenzyl |
| 19 | L-Norleucine | Tert-butyl | 4-Nitrobenzyl |
| 20 | D-Norleucine | Benzyl | 2-Phenylbenzyl |
| 21 | L-Norvaline | | |
| 22 | D-Norvaline | | |
| 23 | L-Aminoisobutyric acid | | |
| 24 | D-Aminoisobutyric acid | | |
| 25 | L-α-Aminobutyric acid | | |
| 26 | L-α-Aminobutyric acid | | |

*Bromide alkylating agents R[3]Br were used except where R[3] = methyl, where methyliodide was used.

EXAMPLE 3
Screening of Libraries in the Kappa Opioid Assay

For screening purposes, the mixtures from the library in Example 2 were combined to create a smaller library composed of a smaller number of mixtures (40 mixtures), each containing a larger number of compounds (26×20=520 compounds each). For example, an equimolar aliquot from each mixture of the library described in Example 2 containing the functional group derived from phenyl isocyanate at the R[2] position was combined. Thus, this new mixture now contained all functional groups at the R[1] position, a defined functionality at the R[2] position, and all functional groups at the R[3] position. This procedure was repeated for each defined R[2] and R[3] functional group to create the 40 mixtures in this library each containing 520 compounds (a mixture of 26 functionalities at the R[1] position; and a mixture of 20 functionalities at the R[3] position when R[2] is defined or a mixture of 20 functionalities at the R[2] position when R[3] is defined).

The library of was screened at 0.1 mg/mL for the ability to inhibit the binding of tritiated U69,593 that is known to bind specifically to the kappa opiate receptor present in guinea pig brain homogenates following literature procedures. [Dooley et al., *J. Biol. Chem.*, 273(30) 18848–18856 (1998).]

Briefly, guinea pig cortices and cerebella were homogenized in 40 mL of Buffer A [50 mM Tris-HCl, pH 7.4] at 4° C. Homogenates were centrifuged [Beckman® J2-HC, 35,300×g] for 10 minutes. The pellets were resuspended in fresh buffer and incubated at 37° C. for 40 minutes. Following incubation, the suspensions were centrifuged as before, the resulting pellets resuspended in 100 volumes of Tris buffer, and the suspensions combined. Membrane suspensions were prepared and used on the same day. Protein content of the crude homogenates was determined by the method of Bradford, *Anal. Biochem.*, 72:248–252 (1976).

Each assay tube contained 0.5 mL of membrane suspension, 3 nm of tritiated U69,593 [(5a,7a,8b)-(−)-N-methyl-N-(7-(1-pyrrolidinyl)-1-oxaspiro(4,5)dec-8-yl) benzeneacetamide; Lahti et al., *European J. Pharmacol.*, 109:281–284(199–85)] in a total volume of 0.65 mL. Assay tubes were incubated for 2.5 hours a 25° C. The assay was then filtered through GF-B filters on a Tomec™ harvester (Orange, Conn.) The filters were subsequently washed with 6 mL of 50 mM Tris-HCl, pH 7.4 at 4° C. Bound radioactivity was counted on a Wallace™ Beta-plate Liquid Scintillation Counter (Piscataway, N.J.). Unlabeled U50,488 [(trans-(dl)-3,4-dichloro-N-methyl-N-[2-(1-pyrrolidinyl) cyclohexyl]benzeneacetamide) methane sulfonate hydrate; Lahti et al., *Life Sci.*, 31:257-xx(1982) and Von Voightlander et al., *J. Pharmacol. Exp. Ther.*, 224:7 (1983)]was used as a competitive inhibitor to generate a standard curve and determine nonspecific binding. The results of these assays are shown in the table, below, wherein the "R" groups shown with an "X" are equimolar mixtures of the substituent "R" groups discussed for Example 2, and those enumerated are the reactant used to provide the particular "R" group.

| # | R[1] | R[2] Reactant | R[3] | Percent Inhibition |
|---|---|---|---|---|
| 1 | X | PhNCO | X | 39.96 |
| 2 | X | 2-methoxy phenyl isocyanate | X | 14.06 |
| 3 | X | 3-methoxy phenyl isocyanate | X | 16.59 |
| 4 | X | 4-methoxy phenyl isocyanate | X | 5.93 |
| 5 | X | o-tolyl isocyanate | X | 15.07 |
| 6 | X | m-tolyl isocyanate | X | 6.54 |
| 7 | X | p-tolyl isocyanate | X | 8.27 |
| 8 | X | 4-fluoro phenyl isocyanate | X | 11.72 |
| 9 | X | 4-chloro phenyl isocyanate | X | 18.33 |
| 10 | X | 4-bromo phenyl isocyanate | X | 7.26 |
| 11 | X | 3-Cl-4-methyl phenyl isocyanate | X | −16.40 |
| 12 | X | 3,4-(methylenedioxy) phenyl-isocyanate | X | −6.25 |
| 13 | X | 4-phenoxy phenyl isocyanate | X | −16.71 |
| 14 | X | 4-ethyl phenyl isocyanate | X | −6.45 |
| 15 | X | α,α,α-trifluoro-p-tolyl isocyanate | X | −4.12 |
| 16 | X | 2,5-dimethyl phenyl isocyanate | X | −7.68 |
| 17 | X | ethyl isocyanate | X | 26.36 |
| 18 | X | butyl isocyanate | X | 19.95 |
| 19 | X | tert-butyl isocyanate | X | −9.90 |
| 20 | X | benzyl isocyanate | X | 8.08 |

| # | R[1] | R[2] | R[3] Reactant | Percent Inhibition |
|---|---|---|---|---|
| 21 | X | X | H (none) | −19.85 |
| 22 | X | X | Iodomethane | 8.39 |
| 23 | X | X | Benzyl bromide | 3.71 |

-continued

| | | | | |
|---|---|---|---|---|
| 24 | X | X | 2-methyl benzyl bromide | 19.55 |
| 25 | X | X | 3-methyl benzyl bromide | 27.37 |
| 26 | X | X | 4-methyl benzyl bromide | 10.01 |
| 27 | X | X | 2-fluoro benzyl bromide | 16.71 |
| 28 | X | X | 3-fluoro benzyl bromide | 12.55 |
| 29 | X | X | 4-fluoro benzyl bromide | 13.67 |
| 30 | X | X | 2-chloro benzyl bromide | 5.55 |
| 31 | X | X | 3-chloro benzyl bromide | −3.09 |
| 32 | X | X | 2,4-difluoro benzyl bromide | 3.41 |
| 33 | X | X | 3,4-difluoro benzyl bromide | −2.99 |
| 34 | X | X | 3,5-difluoro benzyl bromide | 33.47 |
| 35 | X | X | 2,6-difluoro benzyl bromide | 26.87 |
| 36 | X | X | 4-(trifluoromethoxy) benzyl-bromide | 1.57 |
| 37 | X | X | 3-methoxy benzyl bromide | 24.43 |
| 38 | X | X | 3,5-dimethoxy benzyl bromide | −4.61 |
| 39 | X | X | 4-nitro benzyl bromide | −16.50 |
| 40 | X | X | 2-phenyl benzyl bromide | 15.39 |

Each of the patents and articles cited herein is incorporated by reference. The use of the article "a" or "an" is intended to include one or more.

The foregoing description and the examples are is intended as illustrative and are not to be taken as limiting. Still other variations within the spirit and scope of this invention are possible and will readily present themselves to those skilled in the art.

What is claimed:

1. A compound having a structure corresponding to that shown in Formula I, below, or a pharmaceutically acceptable salt thereof:

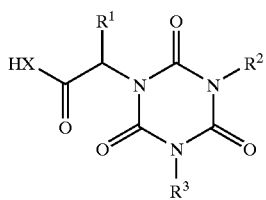

I wherein:

X is O or NH;

$R^1$ is selected from the group consisting of a hydrido, $C_1$–$C_{10}$ alkyl, $C_1$–$C_{10}$ substituted alkyl, $C_7$–$C_{16}$ phenylalkyl, $C_7$–$C_{16}$ substituted phenylalkyl, phenyl, substituted phenyl, $C_3$–$C_7$ cycloalkyl, and a $C_3$–$C_7$ substituted cycloalkyl group;

$R^2$ is selected from the group consisting of a methyl, ethyl, isopropyl, n-propyl, butyl, t-butyl, cyclohexyl, n-octadecyl, phenyl, benzyl, 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 3-chloro-4-methylphenyl, 3-bromo-4-methylphenyl, 3-fluorosulfonylphenyl, 3,4-(methylenedioxy) phenyl, 4-phenoxyphenyl, trans-2-phenylcyclopropyl, 4-toluenesulfonyl, 2-tolyl, 3-tolyl, 4-tolyl, 2-methoxyphenyl, 3-methoxyphenyl, 4-methoxyphenyl, α,α,α-trifluoro-2-tolyl, α,α,α-trifluoro-3-tolyl, α,α,α-trifluoro-4-tolyl, 2,5-dimethylphenyl, 3,4-dimethylphenyl and a 3,5-dimethylphenyl substituent; and $R^3$ is selected from the group consisting of a hydrido, $C_1$–$C_6$ alkyl, $C_2$–$C_6$ alkenyl, benzyl, and a substituted benzyl substituent.

2. The compound according to claim 1 wherein $R^1$ is selected from the group consisting of a hydrido, methyl, benzyl, 2-butyl, N,N-dimethylaminobutyl, N-methylaminobutyl, N-methyl-N-benzylaminobutyl, 2-methylpropyl, methylsulfinylethyl, methylthioethyl, N,N-dimethylaminoethyl, N,N-dimethylaminopropyl, N',N',N'-trimethylguanidinopropyl, N',N',N'-tribenzylguanidinopropyl, N',N'-dibenzylguanidinopropyl, N'-methylguanidinopropyl, hydroxymethyl, 1-hydroxyethyl, 2-propyl, N-methyl-3-indolylmethyl, 4-methoxybenzyl, 4-hydroxybenzyl, propyl, butyl, cyclohexylmethyl, phenyl, 2-naphthylmethyl, and a 4-imidazolylmethyl substituent.

3. The compound according to claim 1 wherein the $R^1$ substituent is a side chain of an amino acid selected from the group consisting of Ala, Phe, Gly, Asp, Asn, Glu, Gln, His, Ile, Lys, Leu, Met, Arg, Nva, Ser, Thr, Val, Trp, Tyr, Nle, Cha, Chg, Fph, Cph, Nph, Aib, Abu, ala, phe, asp, asn, glu, gln, his, ile, lys, leu, met, arg, ser, thr, val, trp, tyr, nle, nva, cha, chg, fph, cph, aib, and abu wherein amino acids written with an initial capital letter are L-amino acids and those written in all lower case letters are D-amino acids.

4. The compound according to claim 1 wherein said compounds have a structure corresponding to that shown in Formulas IIA or IIB below, or a pharmaceutically acceptable salt thereof:

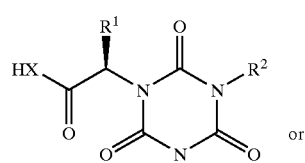

IIA or

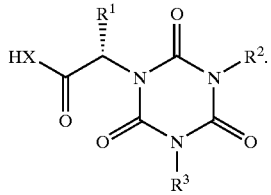

IIB

5. A compound having a structure corresponding to that shown in Formulas IIA or IIB, below, or a pharmaceutically acceptable salt thereof:

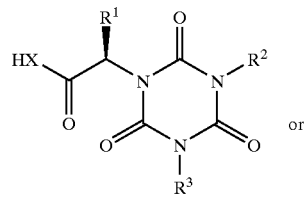

IIA or

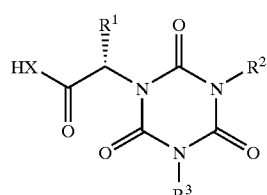

IIB wherein:

X is O or NH;

$R^1$ is selected from the group consisting of a hydrido, methyl, benzyl, 2-butyl, N,N-dimethylaminobutyl, N-methylaminobutyl, N-methyl-N-benzylaminobutyl, 2-methylpropyl, methylsulfinylethyl, methylthioethyl, N,N-dimethylaminoethyl, N,N-dimethylaminopropyl, N',N',N'-trimethylguanidinopropyl, N',N',N'-tribenzylguanidinopropyl, N',N'-dibenzylguanidinopropyl, N'-methylguanidinopropyl, hydroxymethyl, 1-hydroxyethyl, 2-propyl, N-methyl-3-indolylmethyl, 4-methoxybenzyl, 4-hydroxybenzyl, propyl, butyl, cyclohexylmethyl, phenyl, 2-naphthylmethyl, and a 4-imidazolylmethyl substituent;

$R^2$ is selected from the group consisting of a methyl, ethyl, isopropyl, n-propyl, butyl, t-butyl, cyclohexyl, n-octadecyl, phenyl, benzyl, 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 3-chloro-4-methylphenyl, 3-bromo-4-methylphenyl, 3-fluorosulfonylphenyl, 3,4-(methylenedioxy)phenyl, 4-phenoxyphenyl, trans-2-phenylcyclopropyl, 4-toluenesulfonyl, 2-tolyl, 3-tolyl, 4-tolyl, 2-methoxyphenyl, 3-methoxyphenyl, 4-methoxyphenyl, α,α,α-trifluoro-2-tolyl, α,α,α-trifluoro-3-tolyl, α,α,α-trifluoro-4-tolyl, 2,5-dimethylphenyl, 3,4-dimethylphenyl and a 3,5-dimethylphenyl substituent; and $R^3$ is selected from the group consisting of a hydrido, $C_1$–$C_6$ alkyl, $C_2$–$C_6$ alkenyl, benzyl, and a substituted benzyl substituent.

6. The compound according to claim 5 wherein the $R^1$ substituent is a side chain of an amino acid selected from the group consisting of Ala, Phe, Gly, Asp, Asn, Glu, Gln, His, Ile, Lys, Leu, Met, Arg, Nva, Ser, Thr, Val, Trp, Tyr, Nle, Cha, Chg, Fph, Cph, Nph, Aib, Abu, ala, phe, asp, asn, glu, gln, his, ile, lys, leu, met, arg, ser, thr, val, trp, tyr, nle, nva, cha, chg, fph, cph, aib, and abu wherein amino acids written with an initial capital letter are L-amino acids and those written in all lower case letters are D-amino acids.

7. The compound according to claim 5 wherein the $R^2$ substituent is selected from the group consisting of a phenyl, 4-halophenyl, 4-($C_1$–$C_6$-alkyl)phenyl and a $C_1$–$C_6$ alkyl group.

8. The compound according to claim 5 wherein the $R^3$ substituent is selected from the group consisting of a hydrido, methyl, benzyl, 2-, 3- and 4-methylbenzyl, 2-, 3- and 4-fluorobenzyl, 2-, 3- and 4-chlorobenzyl, 2,4-, 3,4-, 3,5- and 2,6-difluorobenzyl, 4-(trifluoromethyl)benzyl, 4-(trifluoromethoxy)benzyl, 2-, 3-, and 4-methoxybenzyl, 3,5- and 3,4-dimethoxybenzyl, 2-, 3- and 4-nitrobenzyl, 2-, 3- and a 4-phenylbenzyl substituent.

* * * * *